United States Patent
Kosugi

(10) Patent No.: US 12,169,948 B2
(45) Date of Patent: Dec. 17, 2024

(54) PROCESSOR FOR ENDOSCOPE, ENDOSCOPE SYSTEM, INFORMATION PROCESSING APPARATUS, NON-TRANSITORY COMPUTER-READABLE STORAGE MEDIUM, AND INFORMATION PROCESSING METHOD

(71) Applicant: HOYA CORPORATION, Tokyo (JP)

(72) Inventor: Kenta Kosugi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 403 days.

(21) Appl. No.: 17/634,394

(22) PCT Filed: Aug. 16, 2019

(86) PCT No.: PCT/JP2019/032131
§ 371 (c)(1),
(2) Date: Feb. 10, 2022

(87) PCT Pub. No.: WO2021/033215
PCT Pub. Date: Feb. 25, 2021

(65) Prior Publication Data
US 2022/0327738 A1  Oct. 13, 2022

(51) Int. Cl.
*G06T 7/80* (2017.01)
*A61B 1/00* (2006.01)
(Continued)

(52) U.S. Cl.
CPC .......... *G06T 7/80* (2017.01); *A61B 1/000096* (2022.02); *G06T 7/90* (2017.01);
(Continued)

(58) Field of Classification Search
CPC ... G06T 7/80; G06T 7/90; G06T 2207/10024; G06T 2207/10068; G06T 2207/20081;
(Continued)

(56) References Cited

U.S. PATENT DOCUMENTS 8,233,037 B2  7/2012  Matsui
2008/0086028 A1*  4/2008  Matsui .................. A61B 1/041
348/45

(Continued)

FOREIGN PATENT DOCUMENTS

JP  2006-288612  10/2006
JP  2011-255038  12/2011
(Continued)

OTHER PUBLICATIONS

Kwitt, R., Uhl, A., Hafner, M., Gangl, A., Wrba, F. and Vecsei, A., Jun. 2010. Predicting the histology of colorectal lesions in a probabilistic framework. In 2010 IEEE Computer Society Conference on Computer Vision and Pattern Recognition—Workshops (pp. 103-110). IEEE.*

(Continued)

*Primary Examiner* — Zhitong Chen
(74) *Attorney, Agent, or Firm* — GREENBLUM & BERNSTEIN, P.L.C.

(57) ABSTRACT

A processor for an endoscope according to an aspect is characterized by including: a controller executing program code to perform: acquiring, by the controller, an endoscopic image captured using first system information; discriminating a part of a subject using a first learning model that outputs a discrimination result of discriminating the part of the subject in a case in which the acquired endoscopic image is input; acquiring, by the controller, a setting image associated with the discrimination result output by the first learning model; and outputting second system information using a second learning model that outputs the second system information in a case in which the acquired setting image and the part of the subject are input.

10 Claims, 22 Drawing Sheets

(51) Int. Cl.
  *G06T 7/90* (2017.01)
  *G06V 10/70* (2022.01)
  *H04N 23/50* (2023.01)
  *H04N 23/74* (2023.01)

(52) U.S. Cl.
  CPC ........ *G06V 10/70* (2022.01); *A61B 1/000094* (2022.02); *A61B 1/000095* (2022.02); *G06T 2207/10024* (2013.01); *G06T 2207/10068* (2013.01); *G06T 2207/20081* (2013.01); *G06T 2207/20084* (2013.01); *G06T 2207/30004* (2013.01); *G06V 2201/03* (2022.01); *H04N 23/555* (2023.01); *H04N 23/74* (2023.01)

(58) Field of Classification Search
  CPC . G06T 2207/20084; G06T 2207/30004; G06T 2207/30028; G06T 2207/30092; G06T 7/0012; A61B 1/000096; A61B 1/000094; A61B 1/000095; A61B 1/00009; A61B 1/045; G06V 10/70; G06V 2201/03; H04N 23/555; H04N 23/74; G16H 30/40; G16H 30/20; G16H 40/40
  See application file for complete search history.

(56) References Cited

U.S. PATENT DOCUMENTS

| | | |
|---|---|---|
| 2014/0184769 A1 | 7/2014 | Ishihara et al. |
| 2015/0245002 A1 | 8/2015 | Kuramoto |
| 2018/0144466 A1 | 5/2018 | Hsieh et al. |
| 2018/0153384 A1 | 6/2018 | Ikemoto et al. |
| 2018/0220873 A1* | 8/2018 | Tani ................ A61B 1/00036 |
| 2018/0325354 A1 | 11/2018 | Saito |
| 2019/0034800 A1 | 1/2019 | Shiratani |
| 2019/0311476 A1 | 10/2019 | Hayami et al. |
| 2019/0374094 A1 | 12/2019 | Yamamoto |
| 2021/0342592 A1* | 11/2021 | Oosake ................ G06T 11/00 |

FOREIGN PATENT DOCUMENTS

| | | |
|---|---|---|
| JP | 2013-56001 | 3/2013 |
| JP | 2014-36738 | 2/2014 |
| JP | 2015-159957 | 9/2015 |
| JP | 2016-158682 | 9/2016 |
| JP | 2016-172077 | 9/2016 |
| JP | 2016-220946 | 12/2016 |
| WO | 2016/208016 | 12/2016 |
| WO | 2017/126425 | 7/2017 |
| WO | 2018/105063 | 6/2018 |
| WO | 2018/159083 | 9/2018 |

OTHER PUBLICATIONS

Liu, D.Y., Gan, T., Rao, N.N., Xing, Y.W., Zheng, J., Li, S., Luo, C.S., Zhou, Z.J. and Wan, Y.L., 2016. Identification of lesion images from gastrointestinal endoscope based on feature extraction of combinational methods with and without learning process. Medical image analysis, 32, pp. 281-294. (Liu).*

Mar. 27, 2023 Extended European Search Report in corresponding European Application No. 19941931.8.

International Search Report Issued in International Patent Application No. PCT/JP2019/032131, dated Nov. 5, 2019, along with an English translation thereof.

* cited by examiner

FIG. 4

| MANAGEMENT ID | IMAGE SETTING | | | | LAMP APERTURE | VOLTAGE/ CURRENT |
|---|---|---|---|---|---|---|
| | RED | BLUE | BRIGHTNESS | ENHANCEMENT | | |
| 001 | 2 | 1 | level3 | Med | ****** | ****** |

FIG. 5

| ITEM ID | CATEGORY | ITEM | DIFFERENCE THRESHOLD VALUE |
|---|---|---|---|
| 001 | IMAGE SETTING | RED | 3 |
| 002 | | BLUE | 3 |
| 003 | | BRIGHTNESS | ****** |
| 004 | | ENHANCEMENT | ****** |
| 005 | LIGHT SOURCE DEVICE | LAMP APERTURE AMOUNT | ****** |
| 006 | | VOLTAGE APPLIED TO THE LAMP | ****** |

FIG.6

| PART ID | SETTING IMAGE ID |
|---------|------------------|
| 001 | 000001 |
| 002 | 000002 |
| 003 | 000003 |

| SETTING IMAGE ID | SETTING IMAGE |
|---|---|
| 000001 | ****** |

FIG.8

| PART ID | PART NAME |
|---|---|
| 001 | MOUTH |
| 002 | ESOPHAGUS |
| 003 | STOMACH |
| 004 | SMALL INTESTINE |
| 005 | LARGE INTESTINE |

277

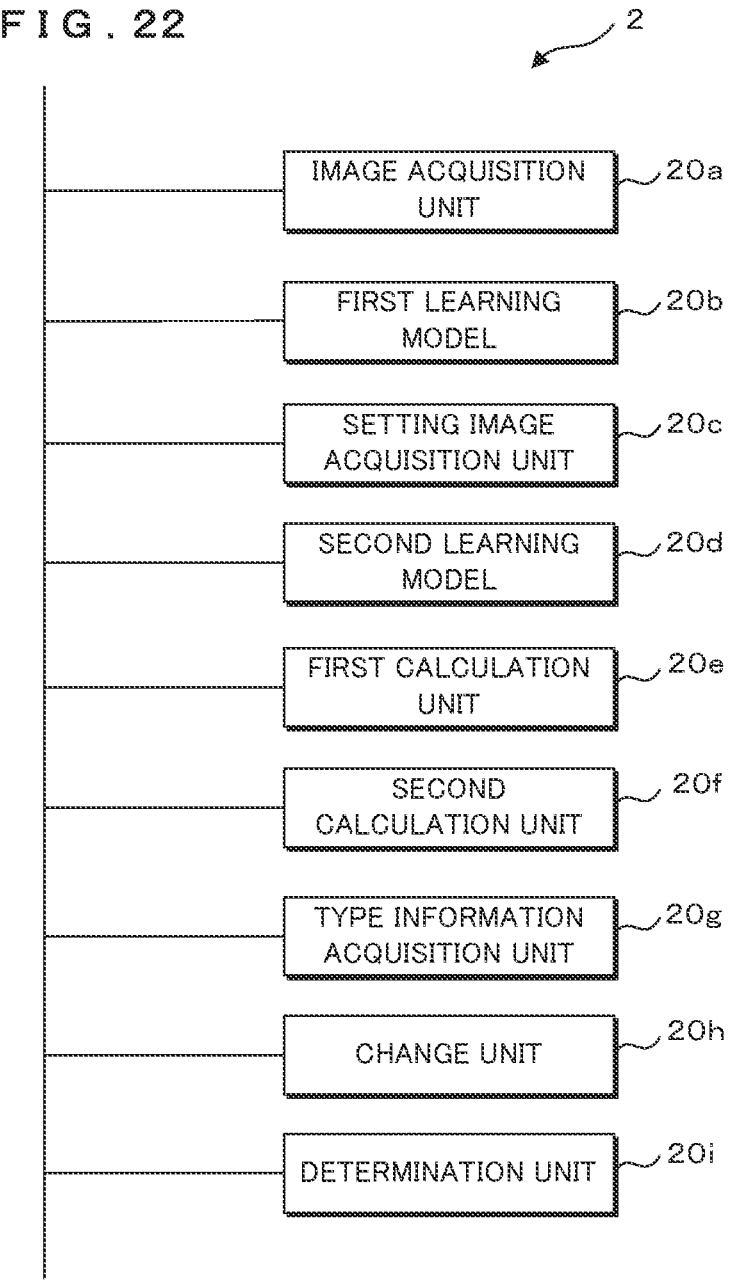

PROCESSOR FOR ENDOSCOPE, ENDOSCOPE SYSTEM, INFORMATION PROCESSING APPARATUS, NON-TRANSITORY COMPUTER-READABLE STORAGE MEDIUM, AND INFORMATION PROCESSING METHOD

CROSS-REFERENCE TO RELATED APPLICATIONS

This application is the national phase under 35 U. S. C. § 371 of PCT International Application No. PCT/JP2019/032131 which has an International filing date of Aug. 16, 2019 and designated the United States of America.

Field

The present disclosure relates to a processor for an endoscope, an endoscope system, an information processing device, a program, and an information processing method.

BACKGROUND

In recent years, there have been various image processing techniques for improving the accuracy of detection in endoscopy. An image processing device that prevents the positional deviation between a mark indicating a site of lesion which is attached to an endoscopic image and the endoscopic image (see Japanese Patent Laid-Open Publication No. 2016-158682, for example).

However, in the invention disclosed in the Japanese Patent Laid-Open Publication No. 2016-158682, in a case in which the type of the endoscope is changed, there is a concern that it will be difficult to reproduce the user's favorite image quality settings.

SUMMARY

A processor for an endoscope according to an aspect is characterized by including: a controller executing program code to perform: acquiring, by the controller, an endoscopic image captured using first system information; discriminating a part of a subject using a first learning model that outputs a discrimination result of discriminating the part of the subject in a case in which the acquired endoscopic image is input; acquiring, by the controller, a setting image associated with the discrimination result output by the first learning model; and outputting second system information using a second learning model that outputs the second system information in a case in which the acquired setting image and the part of the subject are input.

The above and further objects and features will more fully be apparent from the following detailed description with accompanying drawings.

BRIEF DESCRIPTION OF THE DRAWINGS

FIG. 4 is an explanatory diagram illustrating an example of a record layout of a system information DB.

FIG. 5 is an explanatory diagram illustrating an example of a record layout of a threshold value DB.

FIG. 6 is an explanatory diagram illustrating an example of a record layout of a subject DB.

FIG. 7 is an explanatory diagram illustrating an example of a record layout of a setting image DB.

FIG. 8 is an explanatory diagram illustrating an example of a record layout of a part DB.

FIG. 22 is a functional block diagram illustrating the operation of the processor according to Embodiments 1 to 3.

DETAILED DESCRIPTION

Hereinafter, the disclosure will be described in detail with reference to the drawings illustrating embodiments of the disclosure.

Embodiment 1

Figure 1:
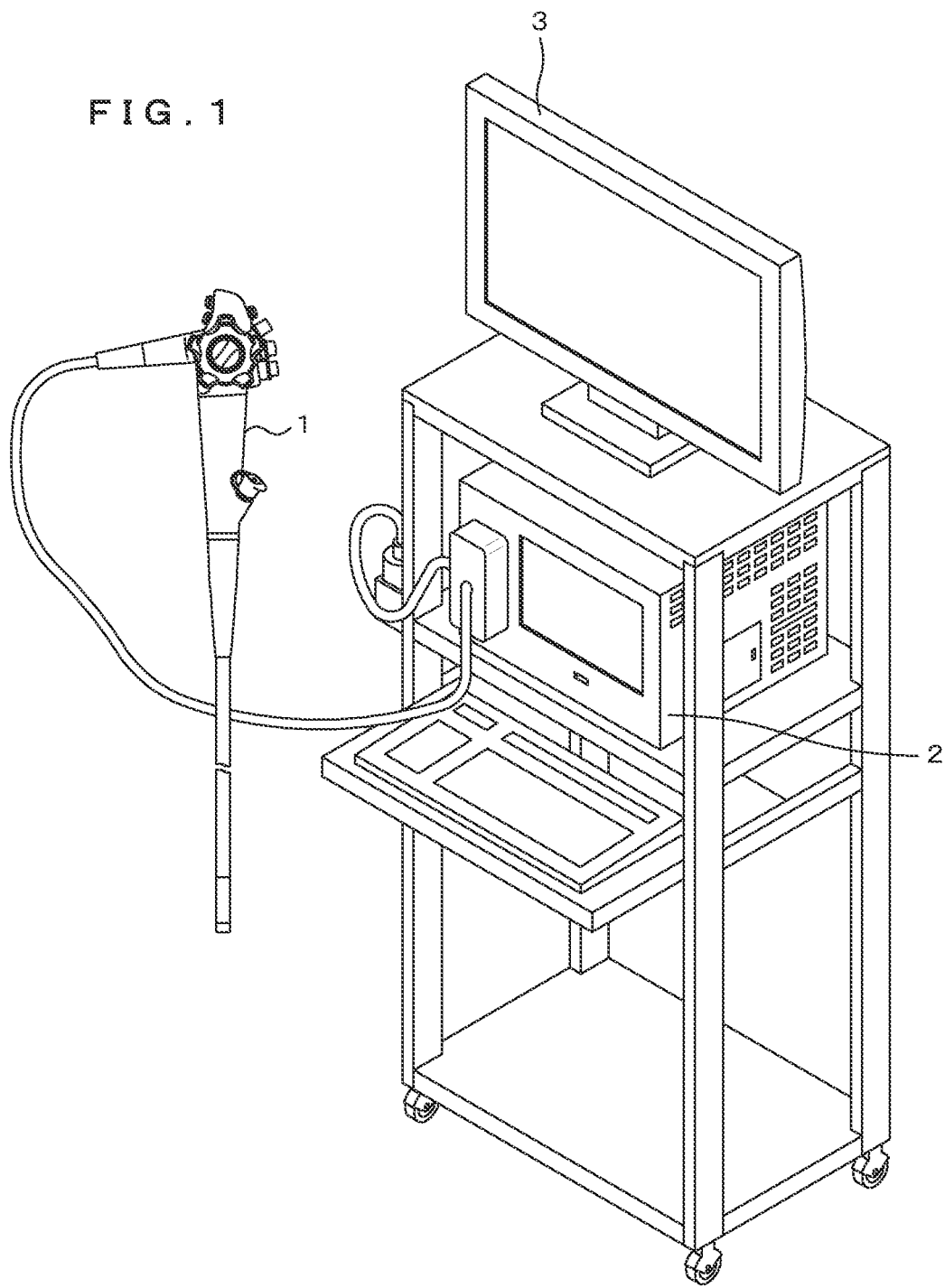
FIG. 1 is a schematic diagram illustrating an example of the configuration of an endoscope system.

Embodiment 1 relates to an aspect in which system settings are automatically adjusted using artificial intelligence (AI). FIG. 1 is a schematic diagram illustrating an example of the configuration an endoscope system. The system illustrated in FIG. 1 includes an endoscope 1 that is inserted into the body of a subject, captures an image, and outputs a video signal to be observed, a processor 2 for an endoscope that converts the video signal output by the endoscope 1 into an endoscopic image, and a display device 3 that displays the endoscopic image and the like. Each device transmits and receives electric signals, video signals, and the like through connectors.

The endoscope 1 is an instrument that includes an insertion portion, which has an imaging element in a tip portion and is inserted into the body of the subject, and is used for diagnosis or treatment. The endoscope 1 transmits the image captured by the imaging element provided at the tip to the processor 2 for an endoscope.

The processor 2 for an endoscope is an information processing device that performs image processing on the captured image acquired from the imaging element provided at the tip of the endoscope 1 to generate an endoscopic image and outputs the endoscopic image to the display device 3. In addition, hereinafter, for the sake of simplicity, the processor 2 for an endoscope is referred to as the processor 2.

The display device 3 is, for example, a liquid crystal display, an organic electroluminescence (EL) display, or the like and displays the endoscopic image or the like output from the processor 2.

Figure 2:
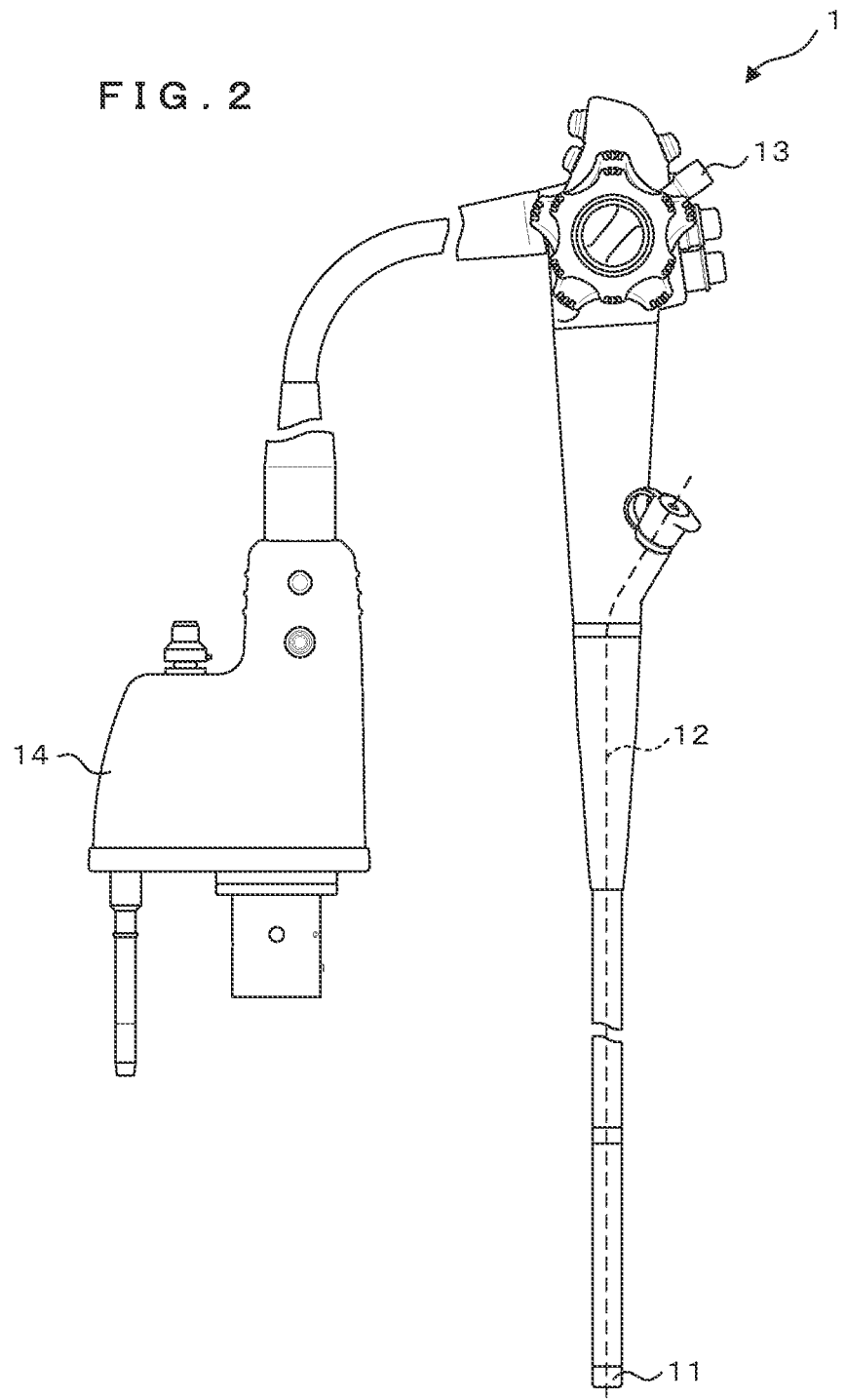
FIG. 2 is a diagram illustrating the outward appearance of an endoscope.

FIG. 2 is a diagram illustrating the outward appearance of the endoscope 1. The endoscope 1 includes an imaging element 11, a treatment tool insertion channel 12, an operation unit 13, and a connector 14. The imaging element 11 is, for example, a charge coupled device (CCD) image sensor, a charge modulation device (CMD) image sensor, or a complementary metal oxide semiconductor (CMOS) image sensor that is installed in the tip portion of the endoscope 1 and performs photoelectric conversion on incident light. A signal processing circuit (not illustrated) performs signal processing, such as A/D conversion and noise removal, on an electric signal generated by the photoelectric conversion and outputs the processed signal to the processor 2.

The treatment tool insertion channel 12 is a channel through which a treatment tool passes. Examples of treatment tool include grippers, biopsy needles, forceps, snares, clamps, scissors, scalpels, incision instruments, endoscopic staplers, tissue loops, clip pliers, suture delivery instruments, energy-based tissue coagulation instruments or tissue cutting instruments. The operation unit 13 is provided with a release button, an angle knob for bending the tip of the endoscope, and the like and receives the input of operation instruction signals from peripheral devices for air supply, water supply, gas supply, and the like. The connector 14 is connected to the processor 2.

Figure 3:
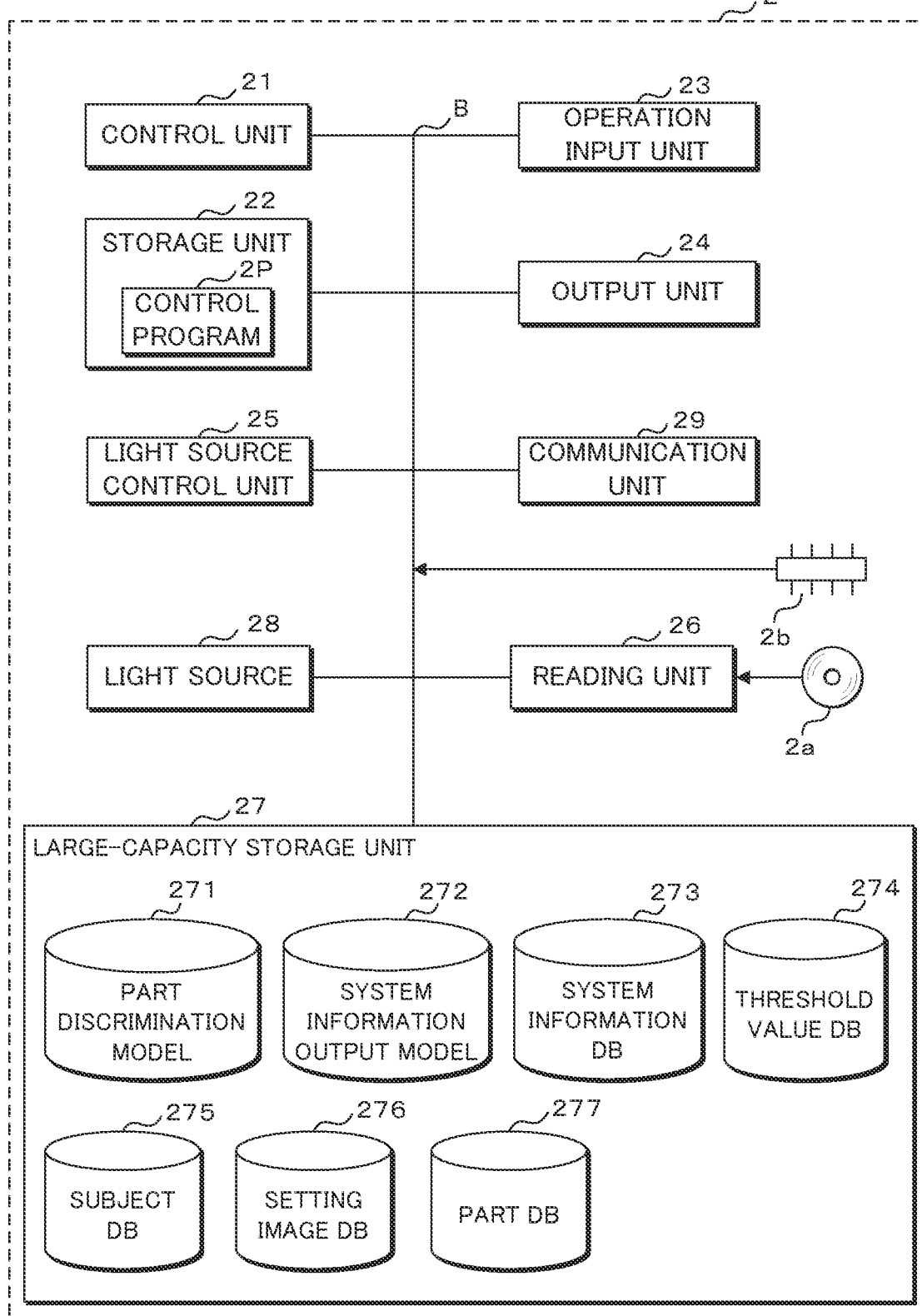
FIG. 3 is a block diagram illustrating an example of the configuration of a processor.

FIG. 3 is a block diagram illustrating an example of the configuration of the processor 2. The processor 2 includes a control unit 21, a storage unit 22, an operation input unit 23, an output unit 24, a light source control unit 25, a reading unit 26, a large-capacity storage unit 27, a light source 28, and a communication unit 29. The components are connected to each other by a bus B.

The control unit 21 includes arithmetic processing units, such as a central processing unit (CPU), a micro-processing unit (MPU), and a graphics processing unit (GPU), reads a control program 2P stored in the storage unit 22, and executes the program 2P to perform various kinds of information processing, a control process, and the like related to the processor 2. In addition, the control unit 21 is described as a single processor in FIG. 3. However, the control unit 21 may be a multiprocessor.

The storage unit 22 includes memory devices, such as a random access memory (RAM) and a read only memory (ROM), and stores the control program 2P or data required for the control unit 21 to execute processes. In addition, the storage unit 22 temporarily stores, for example, data required for the control unit 21 to execute arithmetic processing. The operation input unit 23 includes input devices, such as a touch panel and various switches, and inputs input signals, which have been generated in response to external operations on these input devices, to the control unit 21. The output unit 24 outputs image signals for display and various kinds of information to the display device 3 such that images and information are displayed under the control of the control unit 21.

The light source control unit 25 controls the amount of illumination light emitted by turning on and off LEDs or the like and adjusting a driving current and a driving voltage of the LEDs or the like. In addition, for example, the light source control unit 25 changes an optical filter to control the wavelength band of the illumination light. The light source control unit 25 independently controls the turning-on or turning-off of each LED and the amount of light emitted when each LED is turned on to adjust the emission timing, emission period, amount, and spectrum of the illumination light.

The reading unit 26 reads a portable storage medium 2a including a compact disc (CD)-ROM or a digital versatile disc (DVD)-ROM. The control unit 21 may read the control program 2P from the portable storage medium 2a through the reading unit 26 and store the control program 2P in the large-capacity storage unit 27. In addition, the control unit 21 may download the control program 2P from another computer through a network N or the like and store the control program 2P in the large-capacity storage unit 27. Furthermore, the control unit 21 may read the control program 2P from the semiconductor memory 2b.

The large-capacity storage unit 27 includes, for example, a recording medium such as a hard disk drive (HDD) or a solid state drive (SSD). The large-capacity storage unit 27 stores a part discrimination model (first learning model) 271, a system information output model (second learning model) 272, a system information database (DB) 273, a threshold value DB 274, a subject DB 275, a setting image DB 276, and a part DB 277.

The part discrimination model 271 is a part discriminator that discriminates a part of the subject and is a trained model generated by machine learning. The part of the subject may be, for example, the mouth, the esophagus, the stomach, the small intestine, the large intestine, or the like. The system information output model 272 is an output device that outputs system information and is a trained model generated by machine learning.

The system information DB 273 stores various kinds of system information for setting the system. The threshold value DB 274 stores threshold values of various kinds of system information. The subject DB 275 stores information related to the subject (for example, a patient or the like). The setting image DB 276 stores endoscopic images associated with the part of the subject. The part DB 277 stores the part information of the subject. In addition, the part discrimination model 271 and the system information output model 272 may be disposed in a cloud computing system that is connected through the network and then used.

In addition, in this embodiment, the storage unit 22 and the large-capacity storage unit 27 may be configured as an integrated storage device. Further, the large-capacity storage unit 27 may be composed of a plurality of storage devices. Furthermore, the large-capacity storage unit 27 may be an external storage device that is connected to the processor 2.

The light source 28 includes a light source that emits illumination light used to illuminate the object to be observed. The light source 28 is, for example, semiconductor light sources, such as a plurality of color light emitting diodes (LEDs) having different wavelength ranges, a combination of a laser diode and a phosphor, a xenon lamp, a halogen lamp, or the like. The light used to illuminate the object to be observed is guided to the tip of the endoscope 1 by an optical fiber. In addition, the light source may be provided at the tip of the endoscope. The light source 28 adjusts, for example, brightness under the control of the light source control unit 25 of the processor 2. Further, in this embodiment, the processor 2 is a light source integrated type. However, the disclosure is not limited thereto. For example, the processor 2 may be a light source separated type that is separated from a light source device. The communication unit 29 is a communication module for performing processes related to communication and transmits and receives information to and from, for example, an external information processing device through the network N.

FIG. 4 is an explanatory diagram illustrating an example of the record layout of the system information DB 273. The system information DB 273 is a database that stores a management ID and system information in association with each other. The system information includes, for example, setting information, such as the intensity of a color (for example, red or blue), brightness (luminance), or an enhancement mode for setting the endoscopic image. Further, the system information includes setting information of a lamp aperture for controlling the brightness of the illumination light and the voltage or current applied to a lamp. The above-described information is an example of the system information.

The system information DB 273 includes a management ID column, an image setting column, a lamp aperture column, and a voltage/current column. The management ID column stores the ID of a management number that is uniquely specified, in order to identify the management number for managing each system information item. The image setting column includes a red column, a blue column, a brightness column, and an enhancement column. The red column stores a set value of the intensity of red in the endoscopic image. The blue column stores a set value of the intensity of blue in the endoscopic image. The brightness column stores setting information of the brightness (luminance) of the endoscopic image. For example, in a case in which the brightness is set to 5 levels, "level 1", "level 2", "level 3", "level 4" or "level 5" may be stored in the brightness column.

The enhancement column stores a setting mode for performing an endoscopic image enhancement process on, for example, a structure or a color. The setting mode may be, for example, "Off", "Low", "Med", or "High". For example, the visibility of blood vessels can be improved by emphasizing a difference in color between mucous membranes and blood vessels using color enhancement that emphasizes a minute change in color. The lamp aperture column stores information for controlling the brightness of the illumination light. The voltage/current column stores the voltage or current applied to the lamp.

FIG. 5 is an explanatory diagram illustrating an example of the record layout of the threshold value DB 274. The threshold value DB 274 includes an item ID column, a category column, an item column, and a difference threshold value column. The item ID column stores the ID of an item that is uniquely specified, in order to identify each item. The category column stores type information of the item. The item column stores the name of the item. The difference threshold value column stores a threshold value for determining a difference between each item of first system information and each item of second system information. In addition, the first system information and the second system information will be described below.

FIG. 6 is an explanatory diagram illustrating an example of the record layout of the subject DB 275. The subject DB 275 includes a part ID column and a setting image ID column. The part ID column stores a part ID that specifies a part of the subject. The setting image ID column stores a setting image ID that specifies a setting image (endoscopic image) associated with the part ID.

Figure 7:
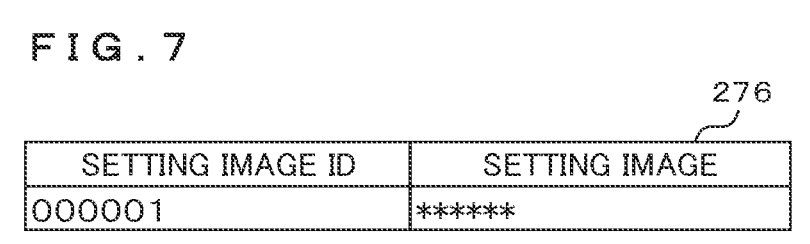

FIG. 7 is an explanatory diagram illustrating an example of the record layout of the setting image DB 276. The setting image is the endoscopic image of each part of the subject captured using the user's (doctor's) favorite image quality settings information. The setting image DB 276 includes a setting image ID column and a setting image column. The setting image ID column stores the ID of the setting image that is uniquely specified, in order to identify each setting image. The setting image column stores data of the setting image.

FIG. 8 is an explanatory diagram illustrating an example of the record layout of the part DB 277. The part DB 277 includes a part ID column and a part name column. The part ID column stores the ID of a part that is uniquely specified, in order to identify each part. The part name column stores the name of the part. For example, the "large intestine" or the "stomach" is stored in the part name column. In addition, for example, a detailed name, such as the "ascending colon" or the "transverse colon", may be stored in the part name column.

Figure 9:
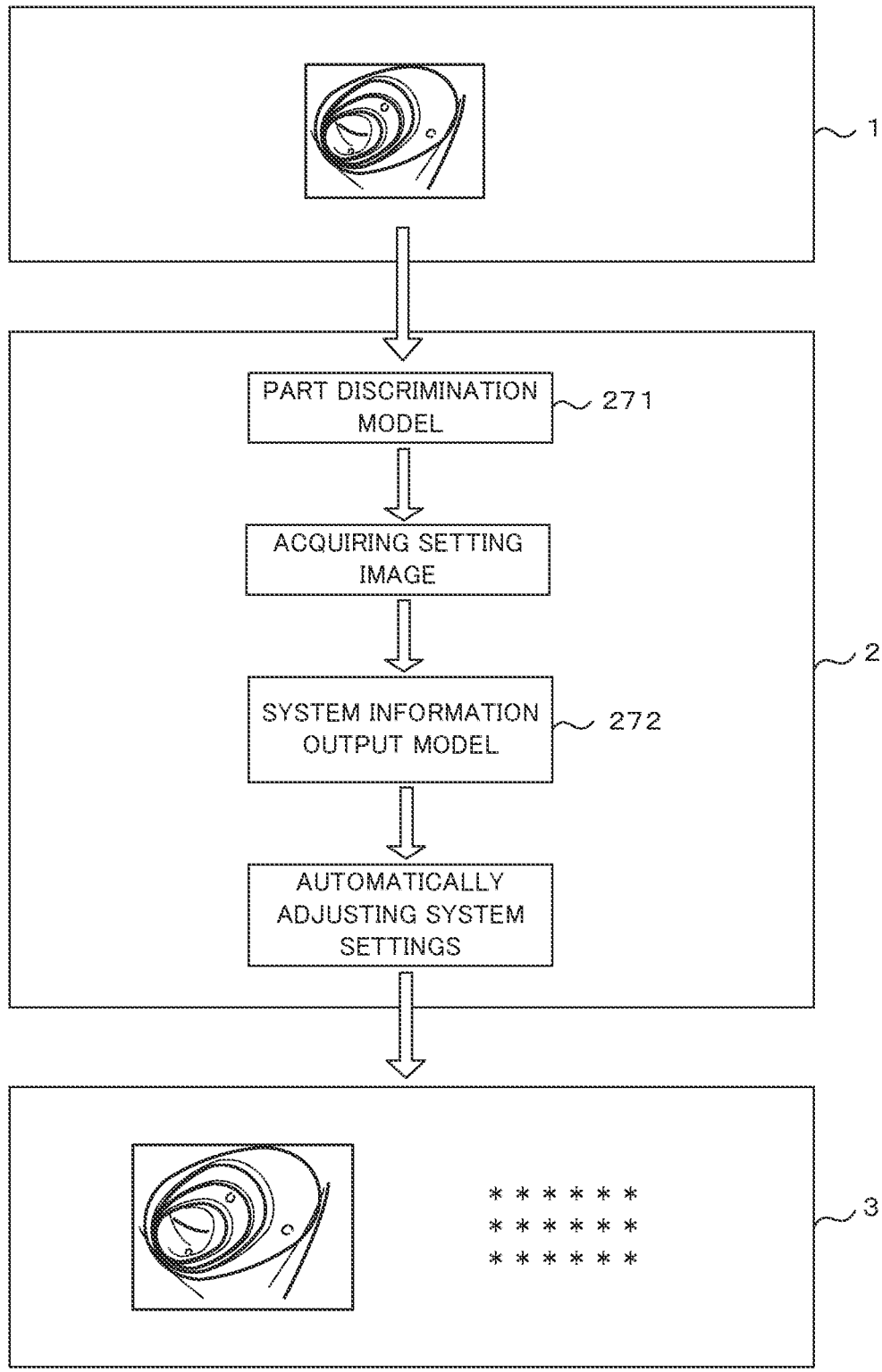
FIG. 9 is an explanatory diagram describing a process of automatically adjusting system settings.

FIG. 9 is an explanatory diagram describing a process of automatically adjusting the system settings. In a case in which the tip of the endoscope 1 is inserted into the body of the subject, the control unit 21 of the processor 2 acquires an endoscopic image captured using the first system information from the endoscope 1. The first system information is system information which has been set in the endoscope system that is being used (currently). The user can operate, for example, a keyboard connected to the processor 2 to change the first system information. In a case in which the first system information is changed, the control unit 21 of the processor 2 stores the first system information in the system information DB 273 of the large-capacity storage unit 27. In addition, since items included in the first system information are the same as the items included in the above-mentioned system information, the description thereof will not be repeated.

The control unit 21 discriminates the part of the subject using the part discrimination model 271 that outputs the discrimination result of discriminating the part of the subject in a case in which the acquired endoscopic image is input. In addition, the part discrimination process will be described below.

The control unit 21 acquires a setting image associated with the discriminated part of the subject. Specifically, the control unit 21 acquires a part ID from the part DB 277 of the large-capacity storage unit 27 on the basis of the discriminated part of the subject. The control unit 21 acquires a setting image ID from the subject DB 275 of the large-capacity storage unit 27 on the basis of the acquired part ID. The control unit 21 acquires a setting image from the setting image DB 276 of the large-capacity storage unit 27 on the basis of the acquired setting image ID.

The control unit 21 acquires (outputs) the second system information using the system information output model 272 that outputs the second system information in a case in which the acquired setting image and the discriminated part of the subject are input. In addition, since items included in the second system information are the same as the items included in the first system information, the description thereof will not be repeated. A process of acquiring the second system information will be described below.

The control unit 21 acquires the first system information from the system information DB 273 of the large-capacity storage unit 27. The control unit 21 compares the acquired first system information with the second system information to determine the difference. Specifically, the control unit 21 compares each item of the first system information with each corresponding item of the second system information for the setting information of the intensity of red, intensity of blue, and brightness of the image, the setting information of the enhancement mode, the setting information of the lamp aperture, and the voltage or current applied to the lamp.

In a case in which the control unit 21 determines that the two information items are not matched with each other, the control unit 21 changes the system setting on the basis of the acquired second system information. For example, in an example in which the intensity of red in the first system information is set to "2", in a case in which the control unit 21 determines that the intensity of red in the second system information is "3", it changes the intensity setting of red in the system to "3". Alternatively, the control unit 21 may change the red intensity setting of the system to an average value (for example, "2.5") of the red intensity.

In addition, for example, in a case in which the control unit 21 determines that the value of the lamp aperture in the second system information is smaller than the value of the lamp aperture in the first system information, it changes the value of the lamp aperture of the system to the value of the lamp aperture in the second system information. In addition, before the system settings are changed, a setting change confirmation message may be output to the user (doctor). In this case, the system settings are changed with the consent of the user.

In a case in which the control unit 21 determines that the change of the system settings has failed, it outputs a notification including the fact that the change has failed to the display device 3. The display device 3 displays the notification including the fact that the change has failed which has been output from the processor 2. In a case in which the control unit 21 determines that the change of the system settings has succeeded, the control unit 21 outputs a notification including the fact that the change has succeeded to the display device 3. The display device 3 displays the notification including the fact that the change has succeeded which has been output from the processor 2.

Figure 10:
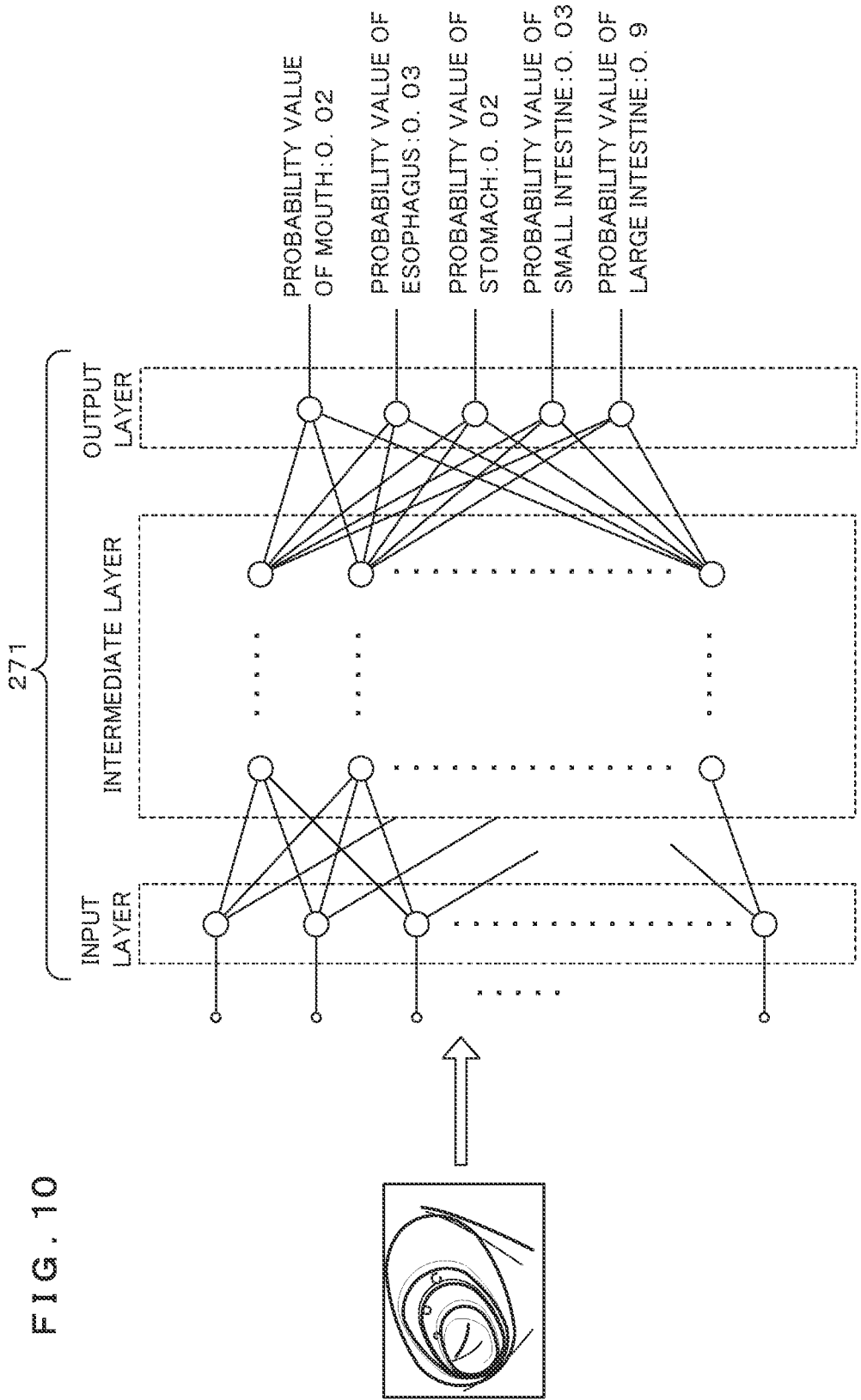
FIG. 10 is an explanatory diagram describing a part discrimination model.

Then, a part discrimination process using the part discrimination model 271 will be described. FIG. 10 is an explanatory diagram describing the part discrimination model 271. The part discrimination model 271 is used as a program module that is a portion of artificial intelligence software. The part discrimination model 271 is a discriminator in which a neural network that receives the endoscopic image captured using the first system information as an input and outputs the result of predicting a part of the subject has been constructed.

The neural network is, for example, a convolutional neural network (CNN) and includes an input layer that receives the input of an endoscopic image, an output layer that outputs the result of predicting a part of the subject, and an intermediate layer that has been trained by backpropagation.

The input layer has a plurality of neurons that receive the input of the pixel values of each pixel included in the endoscopic image and transmits the input pixel values to the intermediate layer. The intermediate layer has a plurality of neurons that extract an image feature amount of the endoscopic image and transmits the extracted image feature amount to the output layer. The intermediate layer finally extracts the feature amount of the image while compressing the pixel information of the endoscopic image, using a configuration in which a convolution layer that convolves the pixel values of each pixel input from the input layer and a pooling layer that maps the pixel values convolved by the convolution layer are alternately connected. Then, the intermediate layer predicts the probability that the endoscopic image will be each part of the subject, using a fully connected layer that has learned the parameter using backpropagation. The prediction result is output to the output layer having a plurality of neurons.

In addition, the endoscopic image may pass through the convolution layer and the pooling layer which are alternately connected such that the feature amount thereof is extracted. Then, the endoscopic image may be input to the input layer.

Further, in this embodiment, the part discrimination model 271 is described as the CNN. However, the part discrimination model 271 is not limited to the CNN and may be a neural network other than the CNN, Regions with Convolutional Neural Networks (R-CNN), Support Vector Machine (SVM), a Bayesian network, or a trained model constructed by any learning algorithm such as a regression tree.

The control unit 21 compares the discrimination result output from the output layer with the labeled information of the part with respect to training data, that is, a correct answer value and optimizes variables used for arithmetic processing in the intermediate layer such that an output value from the output layer is close to the correct answer value. The training data is data that is generated by associating the name of a part (for example, the large intestine) with the endoscopic image. The variables include, for example, a weight (connection coefficient) between neurons and a coefficient of an activation function used in each neuron. A method for optimizing the variables is not particularly limited. For example, the control unit 21 optimizes various variables using a backpropagation method.

The control unit 21 performs the above-described process on each endoscopic image included in the training data to generate the part discrimination model 271. In addition, a process of generating the part discrimination model 271 is not limited to the above-mentioned process. For example, the control unit 21 may generate the part discrimination model for each type of endoscope. For example, the control unit 21 may generate a large intestine discrimination model for discriminating the large intestine.

In this embodiment, an example in which the part discrimination model 271 is generated by the processor 2 has been described. However, the disclosure is not limited to this example. For example, the part discrimination model 271 may be generated by an external device (for example, a server or the like).

In this case, the control unit 21 of the processor 2 may download the part discrimination model 271 generated by the external device using the communication unit 29 and install the part discrimination model 271. In addition, the control unit 21 may read the part discrimination model 271 generated by the external device from the portable storage medium 2a or the semiconductor memory 2b through the reading unit 26 and install the part discrimination model 271. Further, the processor 2 or an external device may perform the process of updating the part discrimination model 271.

Furthermore, the image input to the part discrimination model 271 is not limited to the endoscopic image. For example, as preprocessing, the control unit 21 generates a histogram image indicating the overall distribution of pixel values in the image, a brightness histogram image indicating the brightness distribution of the pixels in the image, a graph image indicating a spatial frequency, or the like on the basis of the endoscopic image. The control unit 21 inputs the generated graph image to the part discrimination model 271, which has been trained by deep learning using the graph image included in the training data, and outputs the discrimination result of discriminating the part of the subject.

In a case in which the control unit 21 acquires the endoscopic image from the endoscope 1, it discriminates the part of the subject using the part discrimination model 271. As illustrated in FIG. 10, the input layer of the part discrimination model 271 receives the input of the endoscopic image and transmits the pixel values of each pixel included in the received endoscopic image to the intermediate layer. The intermediate layer extracts the image feature amount of the endoscopic image from the transmitted pixel values of each pixel. The intermediate layer predicts the probability that the endoscopic image will be each part of the subject on the basis of the extracted image feature amount. The prediction result is output to the output layer having a plurality of neurons. As illustrated in FIG. 10, the prediction result indicating that the probability value of the mouth is 0.02, the probability value of the esophagus is 0.03, the probability value of the stomach is 0.02, the probability value of the small intestine is 0.03, and the probability value of the large intestine is 0.9 is output.

In addition, the part discrimination process is not limited to the process of discriminating the part using machine learning. For example, the control unit 21 of the processor 2 may discriminate the part from the endoscopic image, using a local feature amount extraction method, such as Accelerated KAZE (A-KAZE) or Scale Invariant Feature Transform (SIFT), on the basis of a change in the color or fold of each part. Alternatively, the control unit 21 of the processor 2 may receive the discrimination result of the part of the subject by the doctor on the basis of medical expertise through the operation input unit 23.

Figure 11:
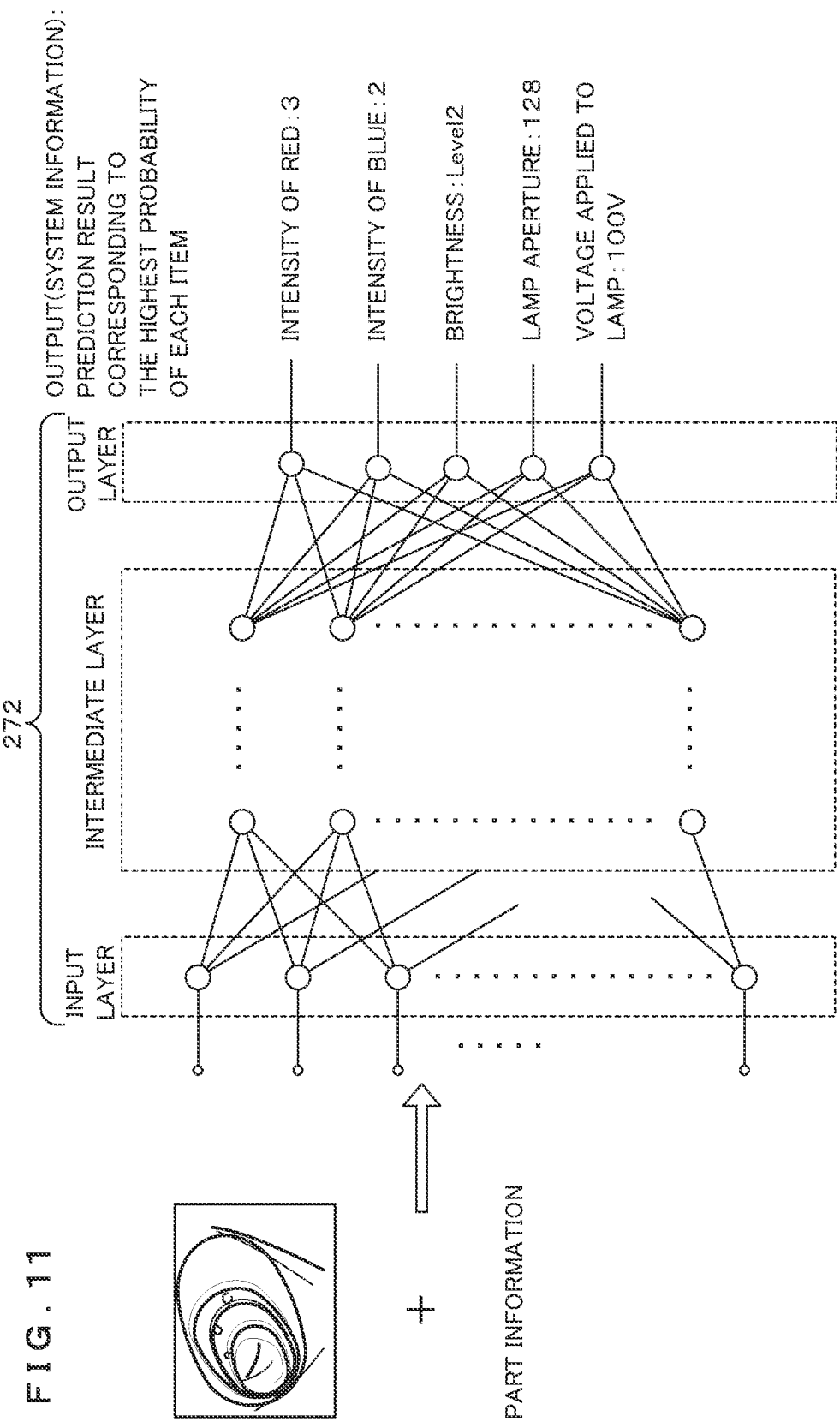
FIG. 11 is an explanatory diagram describing a system information output model.

Next, the process of acquiring the second system information using the system information output model 272 will be described. FIG. 11 is an explanatory diagram describing the system information output model 272. The system information output model 272 is used as a program module that is a portion of artificial intelligence software.

The system information output model 272 is an output device in which a neural network that receives the part of the subject (the discrimination result of the part) output from the part discrimination model 271 and the setting image associated with the part as an input and outputs the result of predicting the second system information has been constructed (generated). Hereinafter, an example in which the neural network is a CNN will be described. Since the configuration of the system information output model 272 in the CNN is the same as the configuration of the part discrimination model 271, the description thereof will not be repeated.

In addition, in this embodiment, the system information output model 272 is described as a CNN. However, the system information output model 272 is not limited to the CNN and may be a neural network other than the CNN, an R-CNN, an SVM, a Bayesian network, or a trained model constructed by any learning algorithm such as a regression tree.

The control unit 21 compares the prediction result output from an output layer with the labeled information of each item of the system information with respect to the training data, that is, the correct answer value and optimizes the variables used for arithmetic processing in an intermediate layer such that the output value from the output layer is close to the correct answer value. The training data is data generated by associating each item of the system information with the setting image and the part of the subject. The control unit 21 performs the above-described process on the setting image and various kinds of information included in the training data to generate the system information output model 272.

Further, the process of generating the system information output model 272 is not limited to the above-described process. For example, the control unit 21 may generate the system information output model for each type of endoscope or may generate the system information output model for each part of the subject. Furthermore, the control unit 21 may generate the system information output model for each item of the system information. For example, the control unit 21 may generate a color intensity determination model for determining the intensity of red or blue of the image, a brightness determination model for determining the brightness of the image, or the like.

Moreover, in this embodiment, an example in which the system information output model 272 is generated by the processor 2 has been described. However, the disclosure is not limited to this example. For example, the system information output model 272 may be generated by an external device.

In a case in which the control unit 21 acquires the part of the subject using the part discrimination model 271, it acquires the second system information using the system information output model 272. An input layer of the system information output model 272 receives the input of the pixel values of each pixel included in the setting image and the part of the subject output from the part discrimination model 271 and transmits the pixel values and the part to the intermediate layer. The intermediate layer extracts the image feature amount of the setting image from the transmitted pixel values of each pixel. The intermediate layer predicts the probability of each item of the system information on the basis of the part of the subject and the extracted image feature amount. The prediction result is output to the output layer having a plurality of neurons.

As illustrated in FIG. 11, the prediction result corresponding to the highest probability of each item of the second system information is output. In addition, the disclosure is not limited to the above-described output result, and all probability values of each item of the system information may be output. Further, the probability values of combinations of the items of the system information may be output. For example, the probability values of "the intensity of red: 3, the intensity of blue: 2, the brightness: Level 2, the lamp aperture: 128, and the voltage applied to the lamp: 100 V" may be output. Furthermore, in addition to outputting the probability values of all combinations, a combination corresponding to the highest probability among the probability values of the combinations may be output as the prediction result.

Figure 12:
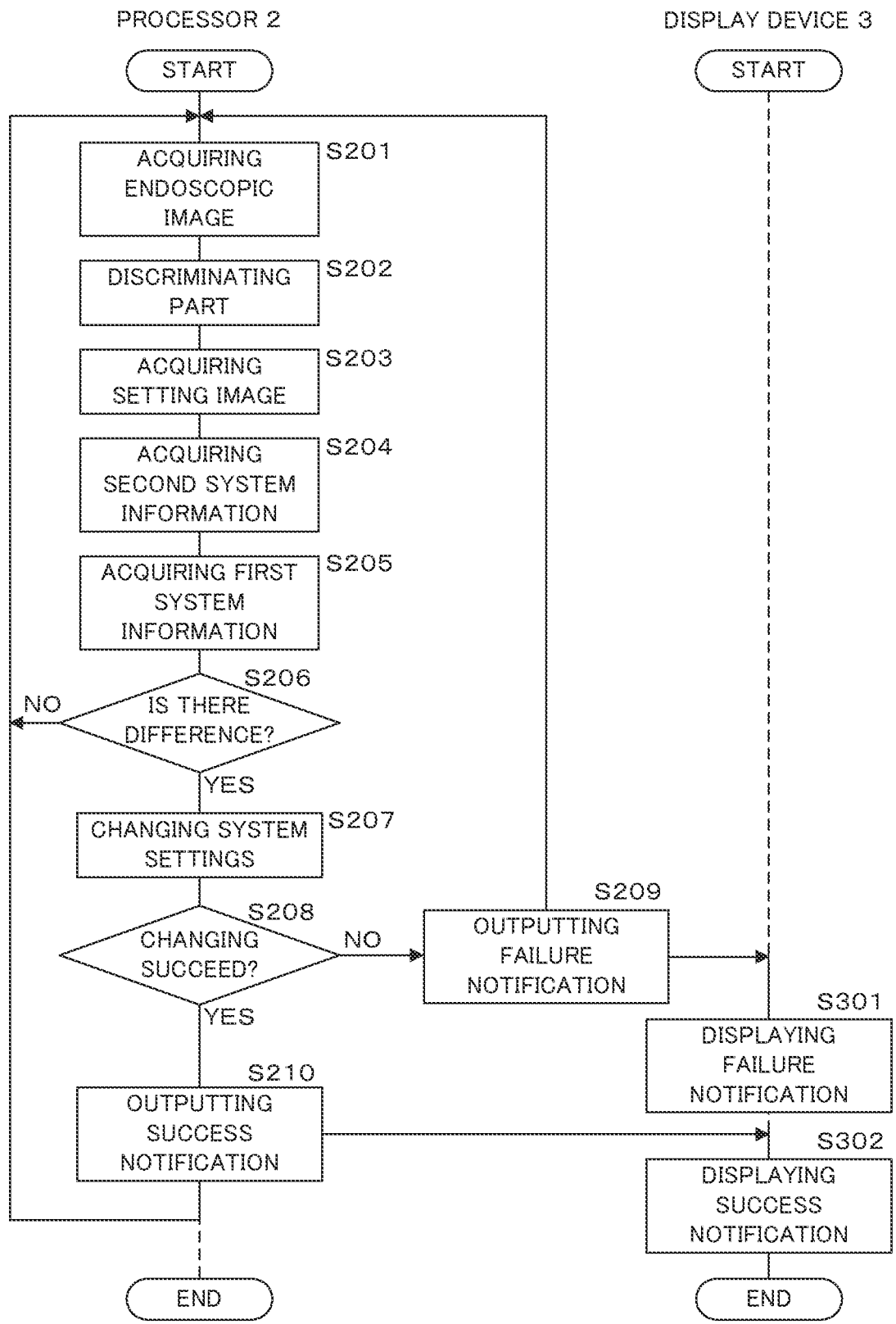
FIG. 12 is a flowchart illustrating a processing procedure when the system settings are automatically adjusted.

FIG. 12 is a flowchart illustrating a processing procedure when the system settings are automatically adjusted. The control unit 21 of the processor 2 acquires the endoscopic image captured using the first system information from the endoscope 1 (Step S201). The control unit 21 discriminates the part of the subject using the part discrimination model 271 that outputs the discrimination result of discriminating the part of the subject in a case in which the acquired endoscopic image is input (Step S202).

The control unit 21 acquires a setting image associated with the part from the setting image DB 276 of the large-capacity storage unit 27 on the basis of the discriminated part of the subject (Step S203). The control unit 21 acquires the second system information using the system information output model 272 that outputs the second system information in a case in which the acquired setting image and the discriminated part of the subject are input (Step S204).

The control unit 21 acquires the first system information including the setting information of the intensity of red, intensity of blue, and brightness of the image, the setting information of the enhancement mode, the setting information of the lamp aperture, and the voltage or current applied to the lamp from the system information DB 273 of the large-capacity storage unit 27 (Step S205). The control unit 21 compares the acquired first system information with the second system information to determine the difference (Step S206).

In a case in which the control unit 21 determines that there is no difference between the first system information and the second system information (NO in Step S206), it returns to Step S201. In a case in which the control unit 21 determines that there is a difference between the first system information and the second system information (YES in Step S206), it changes the system setting on the basis of the acquired second system information (Step S207). The control unit 21 determines whether or not the change of the system settings has succeeded (Step S208).

In a case in which the control unit 21 determines that the change of the system settings has failed (NO in Step S208), the control unit 21 outputs a notification including the fact that the change has failed to the display device 3 (Step S209). For example, in a case in which the values of the items of the second system information are out of the settable range, it is difficult to change the system settings. Therefore, the notification including the fact that the change has failed is output to the display device 3. After outputting the notification, the control unit 21 returns to Step S201. The display device 3 displays the notification including the fact that the change has failed which has been output from the processor 2 (Step S301). In a case in which the control unit 21 determines that the change of the system settings has succeeded (YES in Step S208), it outputs a notification including the fact that the change has succeeded to the display device 3 (Step S210). The display device 3 displays the notification including the fact that the change has succeeded which has been output from the processor 2 (Step S302).

Figure 13A:
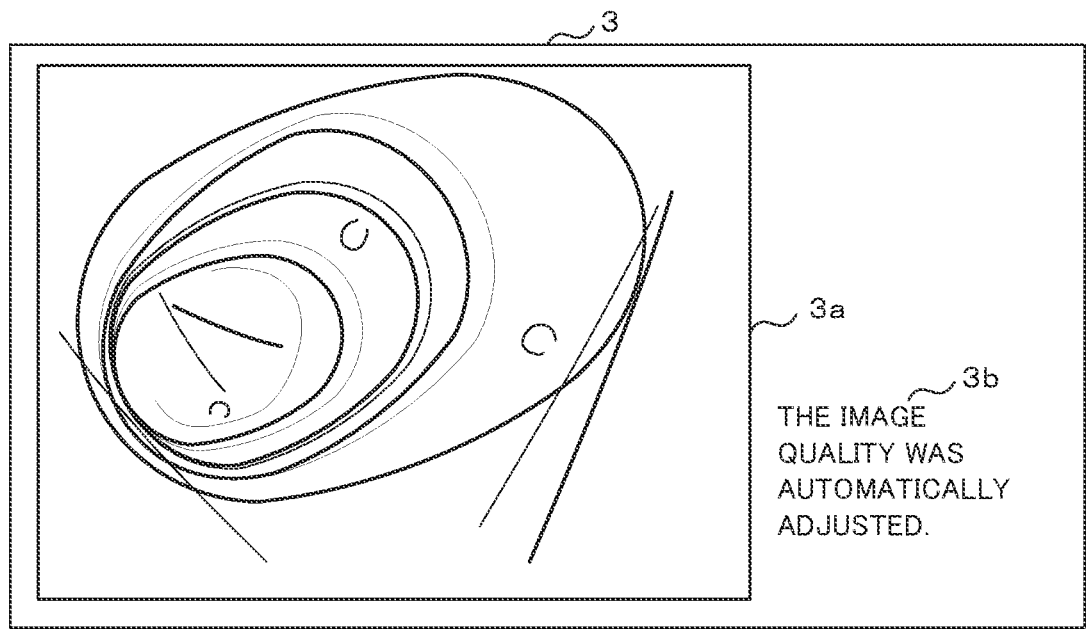
FIG. 13A is a schematic diagram illustrating an endoscopic image on which a notification is displayed by a display device.
Figure 13B:
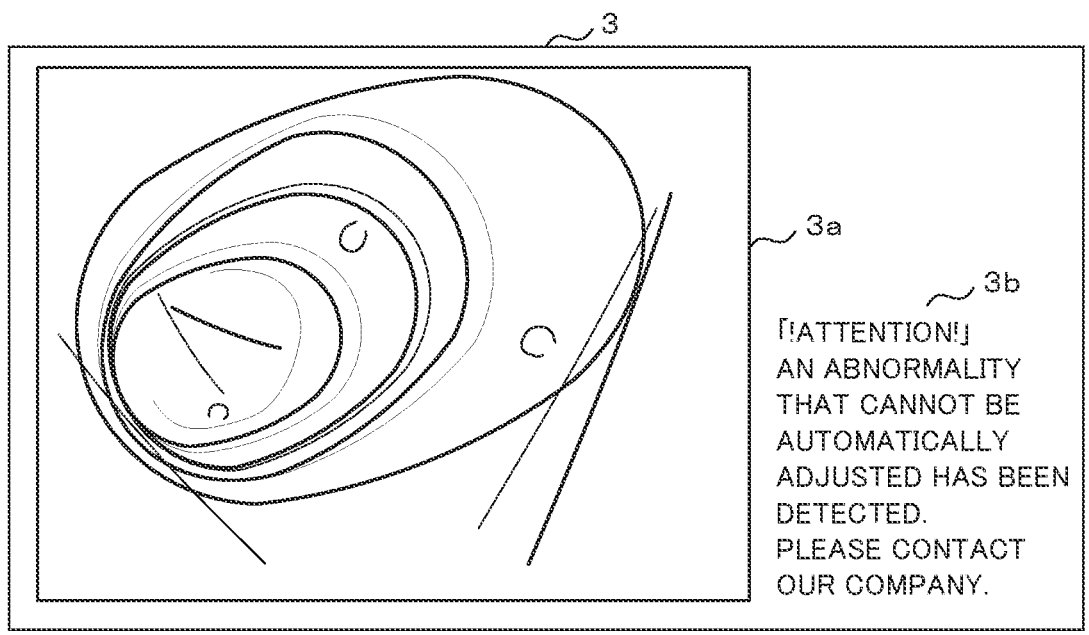
FIG. 13B is a schematic diagram illustrating the endoscopic image on which a notification is displayed by the display device.

FIGS. 13A and 13B are schematic diagrams illustrating the endoscopic image on which the notification is displayed by the display device 3. Observation screen 3*a* is an observation screen (region) of the endoscope. Region 3*b* is a notification (message) display region. The display device 3 displays the endoscopic image output from the processor 2 on the observation screen 3*a* and displays the notification output from the processor 2 in the region 3*b*. In addition, a notification display screen is not limited to the above-described layout. For example, the notification may be displayed so as to be superimposed on the observation screen 3*a* of the endoscope. As illustrated in the drawings, FIG. 13A illustrates an example in which, in a case in which the change of the system settings has succeeded, the notification including the fact that the change has succeeded is displayed. In addition, a recommended change value (for example, a recommended change value of the intensity of red) of the system information to be changed may be output to the display screen. FIG. 13B illustrates an example in which, in a case in which the change of the system settings has failed, the notification including the fact that the change has failed is displayed. In addition to the notification including the fact that the change has failed, for example, the type of target system information whose setting change has failed (for example, the intensity of red or the like) or the changed value used may be output to the display screen.

According to this embodiment, the system settings are automatically adjusted through the learning model using the image feature amount of the setting image prepared in advance, which makes it possible to reproduce the user's favorite image quality settings.

According to this embodiment, it is possible to output a notification indicating that the system settings have been changed.

MODIFICATION EXAMPLE 1

A process of changing the system settings in a case in which the difference between the first system information and the second system information is equal to or greater than a predetermined threshold value will be described. The control unit 21 of the processor 2 determines the difference between the first system information and the second system information output by the system information output model 272. The control unit 21 acquires the threshold value of the difference between the system information items from the threshold value DB 274 of the large-capacity storage unit 27. The control unit 21 determines whether or not the difference between the first system information and the second system information is equal to or greater than the threshold value on the basis of the acquired difference threshold value.

In a case in which the control unit 21 determines that the difference between the first system information and the second system information is equal to or greater than the threshold value, it changes the system setting using the second system information. Hereinafter, an example in which the intensity of red in the first system information is set to "−2" and the intensity of red in the second system information is determined to be "2" will be described. In a case in which the control unit 21 determines that the difference ("4") between the first system information and the second system information is equal to or greater than a predetermined threshold value (for example, "3"), it changes the setting of the intensity of red in the system to "2" on the basis of the second system information.

Figure 14:
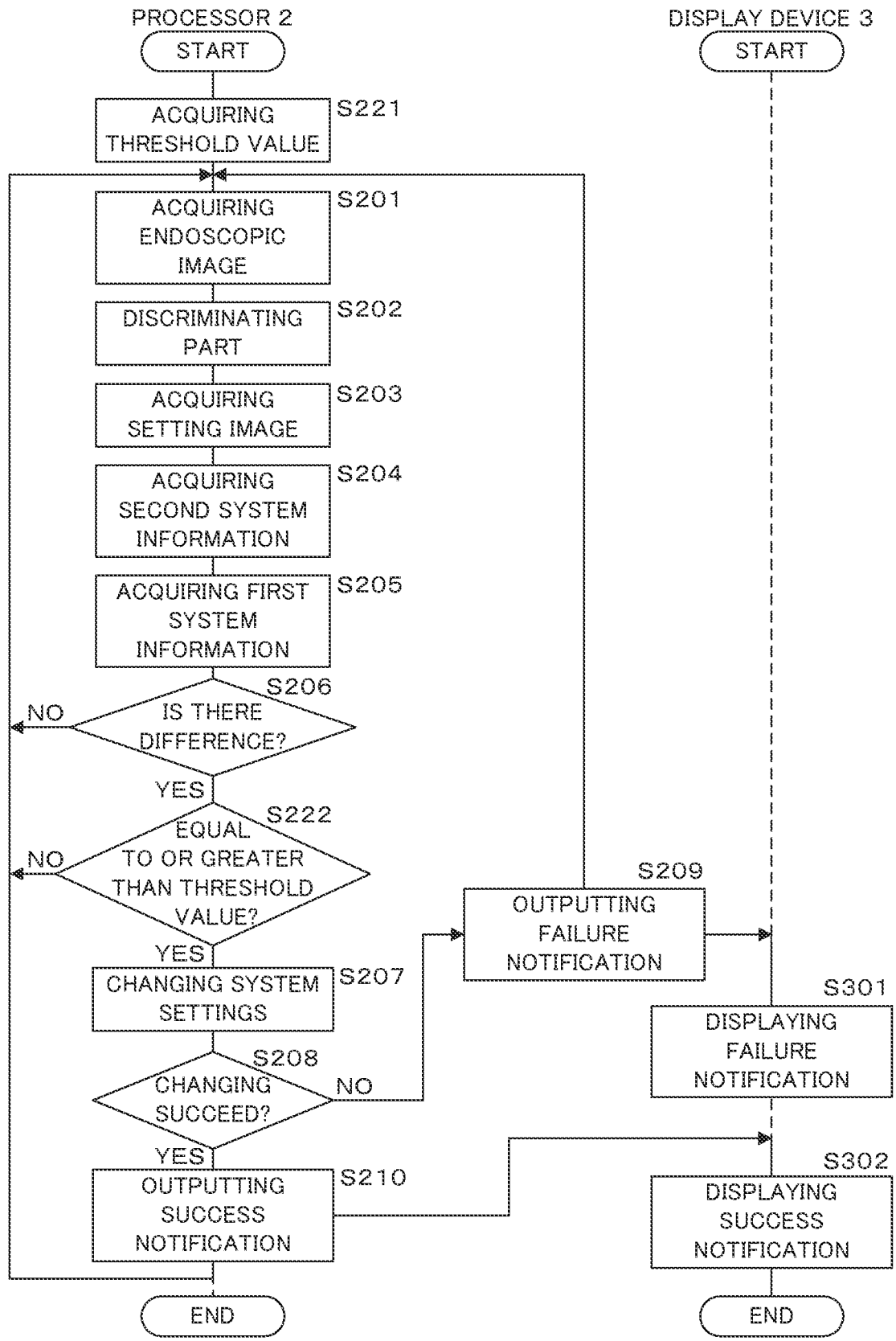
FIG. 14 is a flowchart illustrating a processing procedure when the system settings are automatically adjusted on the basis of a threshold value.

FIG. 14 is a flowchart illustrating a processing procedure when the system settings are automatically adjusted on the basis of the threshold value. In addition, the same content as that in FIG. 12 is denoted by the same reference numeral, and the description thereof will not be repeated. The control unit 21 of the processor 2 acquires the threshold value of the difference between the system information items from the threshold value DB 274 of the large-capacity storage unit 27 (Step S221).

The control unit 21 executes Steps S201 to S206. In a case in which the determination result in Step S206 is "YES", the control unit 21 determines whether or not the difference between the first system information and the second system information is equal to or greater than the threshold value (Step S222). In a case in which the control unit 21 determines that the difference between the first system information and the second system information is not equal to or greater than the threshold value (NO in Step S222), it returns to Step S201. In a case in which the control unit 21 determines that the difference between the first system information and the second system information is equal to or greater than the threshold value (YES in Step S222), it executes Step S207.

According to this modification example, it is determined whether or not to automatically adjust the system settings on the basis of the threshold value. In a case in which the difference is equal to or greater than the threshold value, the system settings are automatically adjusted. On the other hand, in a case in which the difference is equal to or less than the threshold value, the system settings are not automatically adjusted. Therefore, since there is a flexibility in allowing fluctuations in a predetermined range, it is possible to set an appropriate determination rule.

According to this modification example, it is possible to prevent the user from being confused due to too much change in the screen.

Embodiment 2

Embodiment 2 relates to an aspect in which system settings are automatically adjusted by parameter calculated on the basis of an image. In addition, the description of the same content as that in Embodiment 1 will not be repeated.

In a case in which the tip of the endoscope 1 is inserted into the body of the subject, the control unit 21 of the processor 2 acquires the endoscopic image captured using the first system information from the endoscope 1. The control unit 21 calculates first parameter on the basis of the acquired endoscopic image. The first parameter include a color tone parameter, a brightness parameter, a spatial frequency parameter, or a noise amount parameter of the endoscopic image.

The color tone parameter may be, for example, a value obtained by averaging value of R, G, or B pixels values of pixels constituting the endoscopic image within the entire screen or a predetermined range of the screen, or may be the frequency of appearance of the pixel values based on a histogram indicating the overall distribution of the pixel values in the image. R is a pixel value of a red sub-pixel, G is a pixel value of a green sub-pixel, and B is a pixel value of a blue sub-pixel.

The brightness parameter may be, for example, the brightness of each pixel, that is, ((R+G+B)/3) or may be the number of pixels corresponding to each brightness value based on a brightness histogram indicating the brightness distribution of the pixels in the image and the degree of bias of the distribution.

The spatial frequency parameter may be, for example, the frequency distribution of image data obtained by the Fourier transform. The spatial frequency indicates the number of repetitions of a pattern included in a unit length. For example, the spatial frequency indicates the number of repetitions of a sinusoidal shading change per unit length for a two-dimensional image. In this case, the spatial frequency is high in the place where shading changes rapidly and is low in the place where the shading changes slowly.

The noise amount parameter is the amount of image noise and is represented by the standard deviation (SD) which is the square root of the variance. The image noise is a high-frequency component having a high spatial frequency in brightness non-uniformity that occurs in the captured image. The standard deviation is represented by a value indicating the degree of scattering of data.

The control unit 21 acquires the type information of the endoscope 1. The type information includes, for example, the series and model number of the endoscope, the number of pixels of the imaging element, and target part information (for example, the upper gastrointestinal tract). The control unit 21 acquires the type information from the endoscope 1 (scope). Alternatively, in a case in which type information corresponding to each model number is stored in the storage unit 22 in advance, the control unit 21 acquires the model number from the endoscope 1. The control unit 21 may acquire type information corresponding to the acquired model number from the storage unit 22.

The control unit 21 discriminates the part of the subject using the part discrimination model 271 that outputs the discrimination result of discriminating the part of the subject in a case in which the first parameter calculated on the basis of the endoscopic image and the acquired type information are input. In addition, a part discrimination process will be described below.

The control unit 21 acquires a setting image associated with the discriminated part of the subject. In addition, since a process of acquiring the setting image is the same as that in Embodiment 1, the description thereof will not be repeated. The control unit 21 calculates second parameter on the basis of the acquired setting image. Further, since various parameters included in the second parameter are the same as the various parameters included in the first parameter, the description thereof will not be repeated.

The control unit 21 acquires the second system information using the system information output model 272 that outputs the second system information in a case in which the second parameter calculated on the basis of the setting image, the acquired type information, and the discriminated part of the subject are input. In addition, a process of acquiring the second system information will be described below.

A process of determining the difference between the first system information and the second system information and a process of changing the system settings after the second system information is acquired are the same as those in Embodiment 1. Therefore, the description thereof will not be repeated.

Figure 15:
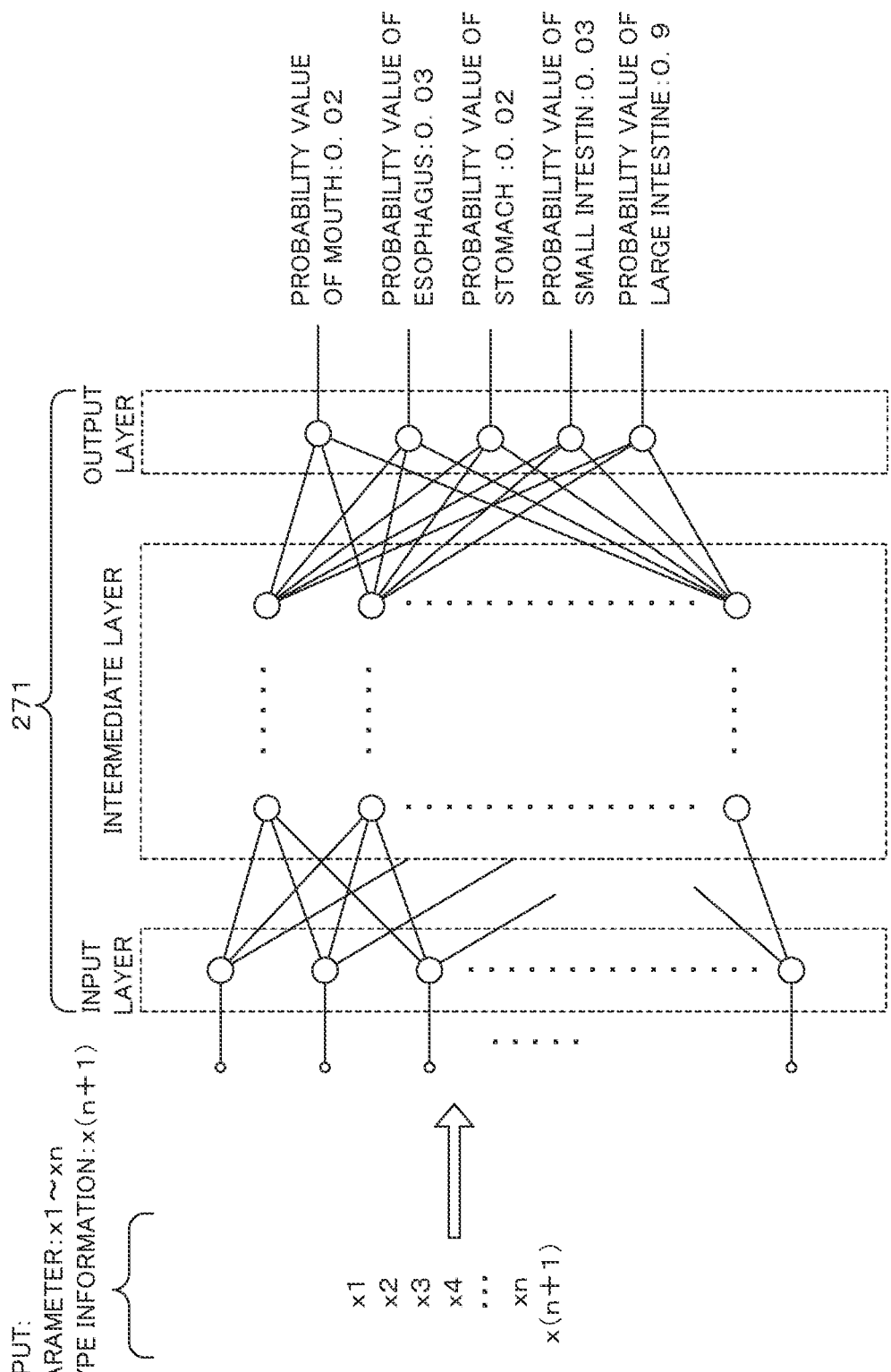
FIG. 15 is an explanatory diagram describing a part discrimination model according to Embodiment 2.

Then, the part discrimination process using the part discrimination model 271 will be described. FIG. 15 is an explanatory diagram describing the part discrimination model 271 according to Embodiment 2. The part discrimination model 271 according to this embodiment is a discriminator in which a neural network that receives parameter calculated on the basis of an endoscopic image and type information as an input and outputs the result of predicting a part of the subject has been constructed (generated).

The neural network is, for example, a CNN and includes an input layer that receives the input of the parameter calculated on the basis of the endoscopic image and the type information, an output layer that outputs the result of predicting a part of the subject, and an intermediate layer that has been trained by backpropagation. Each layer has one or more neurons (nodes), and each neuron has a value. Then, the neurons between one layer and the next layer are connected by edges, and each edge has variables (or parameter) such as weights or biases.

In the CNN, the value of the neuron in each layer is calculated by performing predetermined computation based on, for example, the value of the neuron in the previous layer and the weight of the edge. Then, when the input data is input to the neuron of the input layer, the value of the neuron in the next layer is calculated by predetermined computation. Further, when the data calculated by computation is input, the value of the neuron in the next layer is calculated by predetermined computation in the layer. Then, the value of the neuron in the output layer which is the last layer becomes output data with respect to the input data.

The control unit 21 compares the discrimination result output from the output layer with the labeled information of the part with respect to training data, that is, a correct answer value and optimizes the variables used for arithmetic processing in the intermediate layer such that an output value from the output layer is close to the correct answer value. The training data is data that is generated by associating the name of a part (for example, the large intestine) with the parameter calculated on the basis of the endoscopic image and the type information of the endoscope 1. The control unit 21 performs the above-described process on the parameter and the type information included in the training data to generate the part discrimination model 271.

In a case in which the control unit 21 acquires the endoscopic image from the endoscope 1, it calculates parameter on the basis of the acquired endoscopic image. The control unit 21 discriminates the part of the subject using the part discrimination model 271 on the basis of the calculated parameter. As illustrated in FIG. 15, the input layer of the part discrimination model 271 receives the input of parameter "x1 to xn" calculated on the basis of the endoscopic image and type information "x(n+1)". x1 to xn indicate the color tone parameter, the brightness parameter, the spatial frequency parameter, or the noise amount parameter of the above-mentioned endoscopic image. x(n+1) indicates type information including the series and model number of the endoscope, the number of pixels of the imaging element, or target part information.

In addition, in the above-described various parameter, in a case in which the average value of R, G, or B pixels values of pixels constituting the endoscopic image, the degree of bias of the distribution based on the histogram, or the spatial frequency is input to the part discrimination model 271, the parameter has a great influence on the discrimination result of the part of the subject.

The intermediate layer changes the number of dimensions of input information input from the input layer to extract the features of the input information. Then, the intermediate layer predicts the probability that the endoscopic image will be each part of the subject corresponding to the extracted features using a fully connected layer that has learned parameter using backpropagation. The prediction result is output to the output layer having a plurality of neurons. As illustrated in FIG. 15, the prediction result indicating that the probability value of the mouth is 0.02, the probability value of the esophagus is 0.03, the probability value of the stomach is 0.02, the probability value of the small intestine is 0.03, and the probability value of the large intestine is 0.9 is output.

Figure 16:
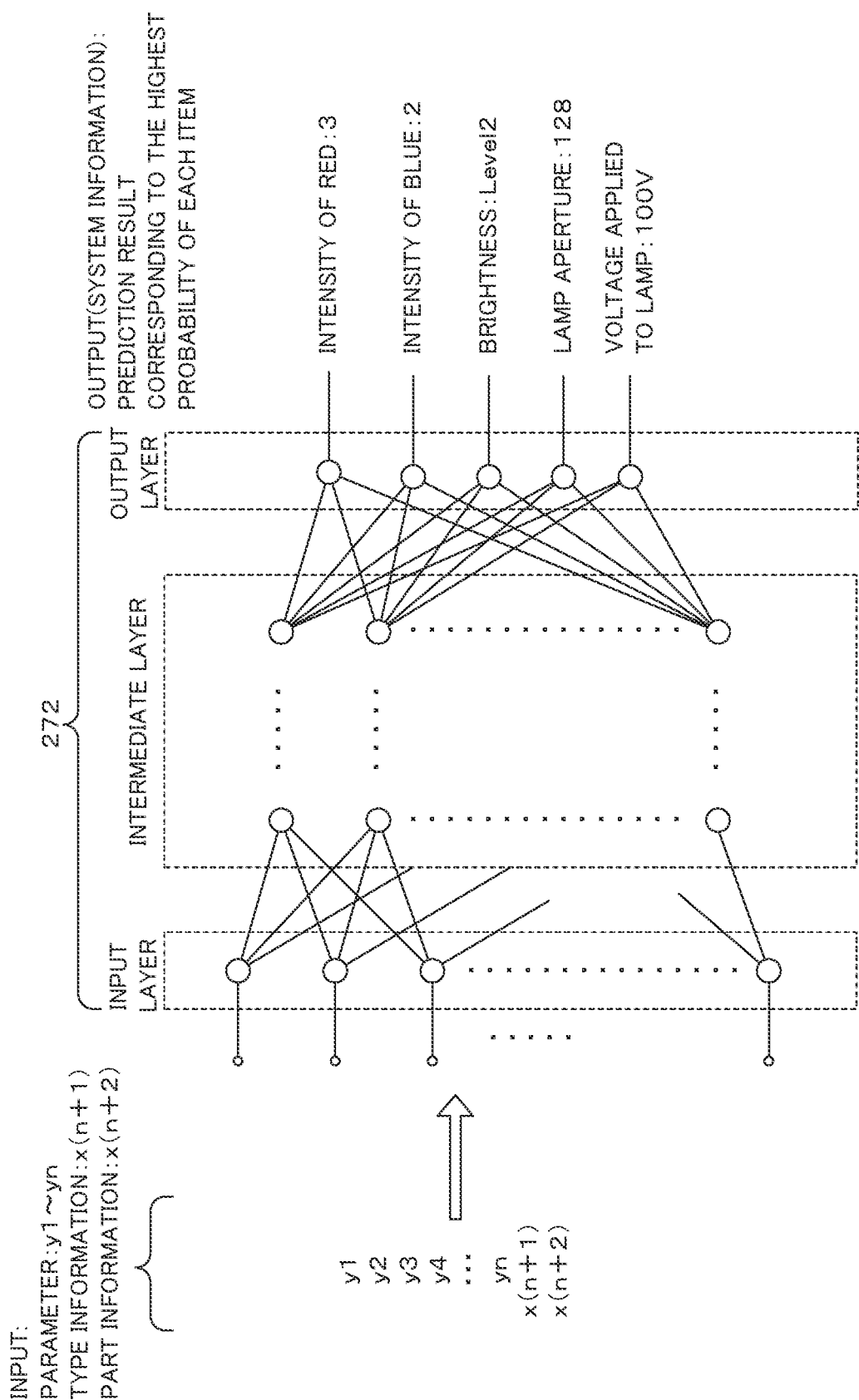
FIG. 16 is an explanatory diagram describing a system information output model according to Embodiment 2.

Then, a process of acquiring the second system information using the system information output model 272 will be described. FIG. 16 is an explanatory diagram describing the system information output model 272 according to Embodiment 2.

The system information output model 272 is an output device in which a neural network that receives the parameter calculated on the basis of the setting image, the type information, and the part of the subject (the discrimination result of the part) output from the part discrimination model 271 as an input and outputs the result of predicting the second system information has been constructed (generated). Hereinafter, an example in which the neural network is a CNN will be described. In addition, since the configuration of the system information output model 272 in the CNN is the same as the configuration of the part discrimination model 271, the description thereof will not be repeated.

The control unit 21 compares the prediction result output from the output layer with the labeled information of each item of the system information with respect to training data, that is, the correct answer value and optimizes the variables used for arithmetic processing in the intermediate layer such that the output value from the output layer is close to the correct answer value. The training data is data generated by associating each item of the system information with the parameter calculated on the basis of the setting image, the type information of the endoscope 1, and the part of the subject. The control unit 21 performs the above-described process on the parameter and various kinds of information included in the training data to generate the system information output model 272.

In a case in which the control unit 21 acquires the part of the subject using the part discrimination model 271, it acquires a setting image associated with the acquired part of the subject. The control unit 21 calculates parameter on the basis of the acquired setting image. The control unit 21 acquires the second system information using the system information output model 272 on the basis of the calculated parameter. As illustrated in FIG. 16, the input layer of the system information output model 272 receives the input of parameter "y1 to yn" calculated on the basis of the setting image, type information "x(n+1)", and a part "x(n+2)" of the subject output from the part discrimination model 271.

y1 to yn indicate the color tone parameter, the brightness parameter, the spatial frequency parameter, or the noise amount parameter of the above-mentioned setting image. x(n+1) indicates type information including the series and model number of the endoscope, the number of pixels of the imaging element, or target part information. x(n+2) indicates a part (for example, the large intestine) of the subject.

In addition, in the above-described various parameters, in a case in which the frequency of appearance of the pixel values based on a histogram, the average value of brightness, or the amount of noise (standard deviation) is input to the system information output model 272, the parameter has a great influence on the output result of the second system information.

The intermediate layer changes the number of dimensions of input information input from the input layer to extract the features of the input information. Then, the intermediate layer predicts the probability of each item of the second system information corresponding to the extracted features, using the fully connected layer that has learned parameter using backpropagation. The prediction result is output to the output layer having a plurality of neurons.

Figure 17:
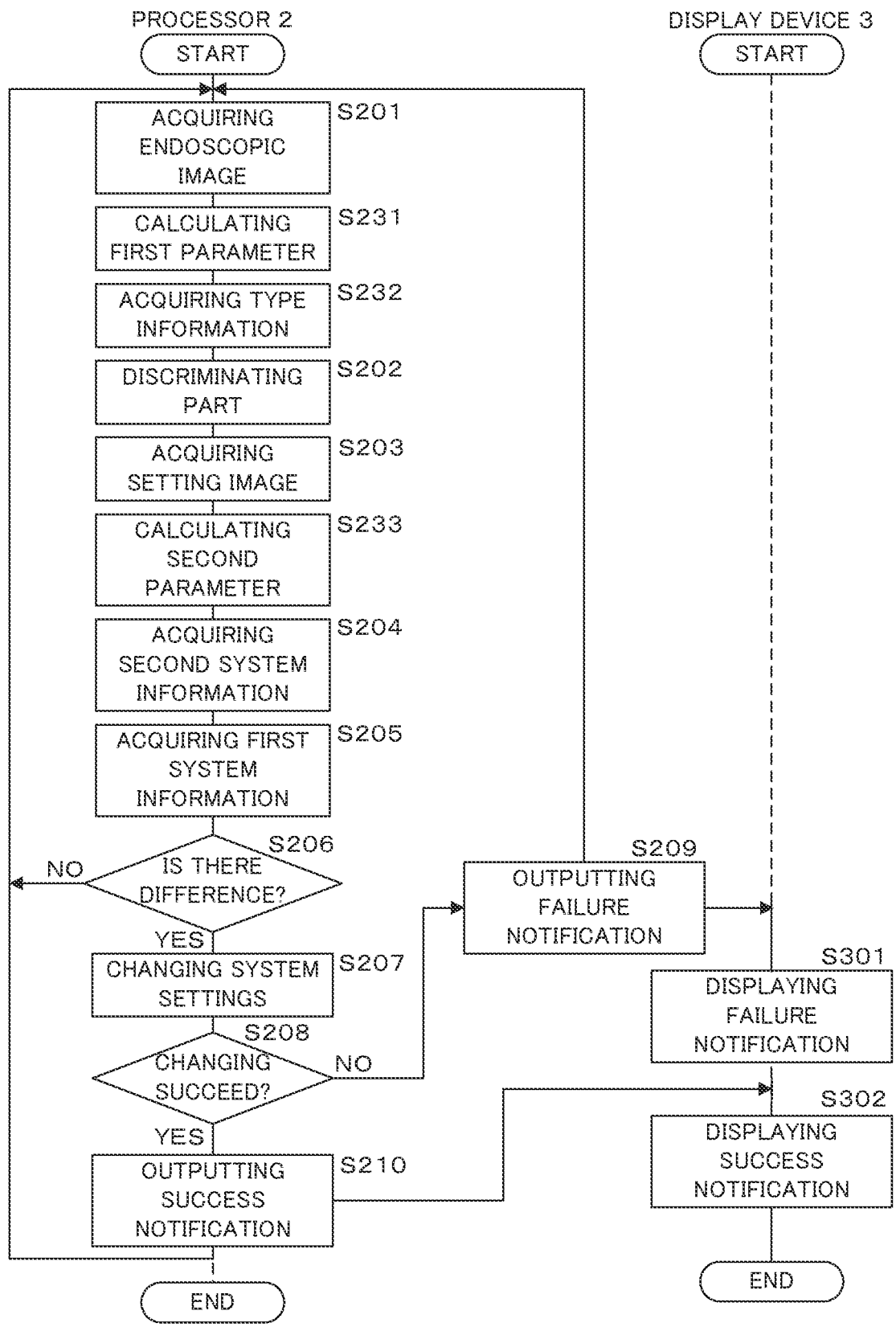
FIG. 17 is a flowchart illustrating a processing procedure when the system settings are automatically adjusted in Embodiment 2.

FIG. 17 is a flowchart illustrating a processing procedure when the system settings are automatically adjusted in Embodiment 2. The same content as that in FIG. 12 is denoted by the same reference numeral, and the description thereof will not be repeated. After executing Step S201, the control unit 21 of the processor 2 calculates the first parameter on the basis of the acquired endoscopic image (Step S231).

The control unit 21 acquires the type information of the endoscope including, for example, a series, a model number, the number of pixels of the imaging element, and target part information stored in the endoscope 1 in advance (Step S232). After executing Steps S202 and S203, the control unit 21 calculates the second parameter on the basis of the acquired setting image (Step S233). The control unit 21 executes Step S204.

According to this embodiment, it is possible to output system information in a case in which various parameters, such as image settings, an optical system, a light source, and electricity, that affect image quality are input to a learning model.

Embodiment 3

Embodiment 3 relates to an aspect in which a setting image is stored in association with part information. In addition, the description of the same content as that in Embodiments 1 and 2 will not be repeated. The endoscopic image of the subject captured for each part can be stored as a setting image in the large-capacity storage unit 27.

Figure 18:
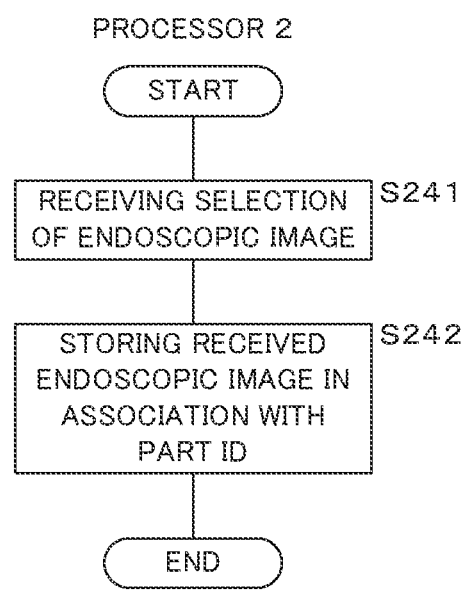
FIG. 18 is a flowchart illustrating a processing procedure when a setting image is stored.

FIG. 18 is a flowchart illustrating a processing procedure in a case in which the setting image is stored. The control unit 21 of the processor 2 receives the selection of the endoscopic image obtained by capturing the part of the subject (Step S241). The control unit 21 stores the received endoscopic image in the large-capacity storage unit 27 in association with the part ID (Step S242). Specifically, the control unit 21 allocates a setting image ID, stores the setting image as one record in the setting image DB 276 so as to be associated with the setting image ID. The control unit 21 stores the part ID and the setting image ID as one record in the subject DB 275.

According to this embodiment, the endoscopic image obtained by capturing a part of the subject is stored in association with the part information, which makes it possible to provide data in the construction of the part discrimination model 271 or the discrimination process.

Embodiment 4

Embodiment 4 relates to an aspect in which an information processing device 4 automatically adjusts system settings using artificial intelligence. In addition, the description of the same content as that in Embodiments 1 to 3 will not be repeated. In Embodiment 1 or 2, the processor 2 performs the part discrimination process and the second system information output process using the learning model. However, in this embodiment, an aspect in which the above-described processes are performed by the information processing device 4 will be described.

The information processing device 4 is an information processing device that constructs a learning model, outputs system information using the learning model, and performs the processing, storage, transmission, and reception of various kinds of information. The information processing device 4 is, for example, a server device, a personal computer, a general-purpose tablet PC (personal computer), or the like.

Figure 19:
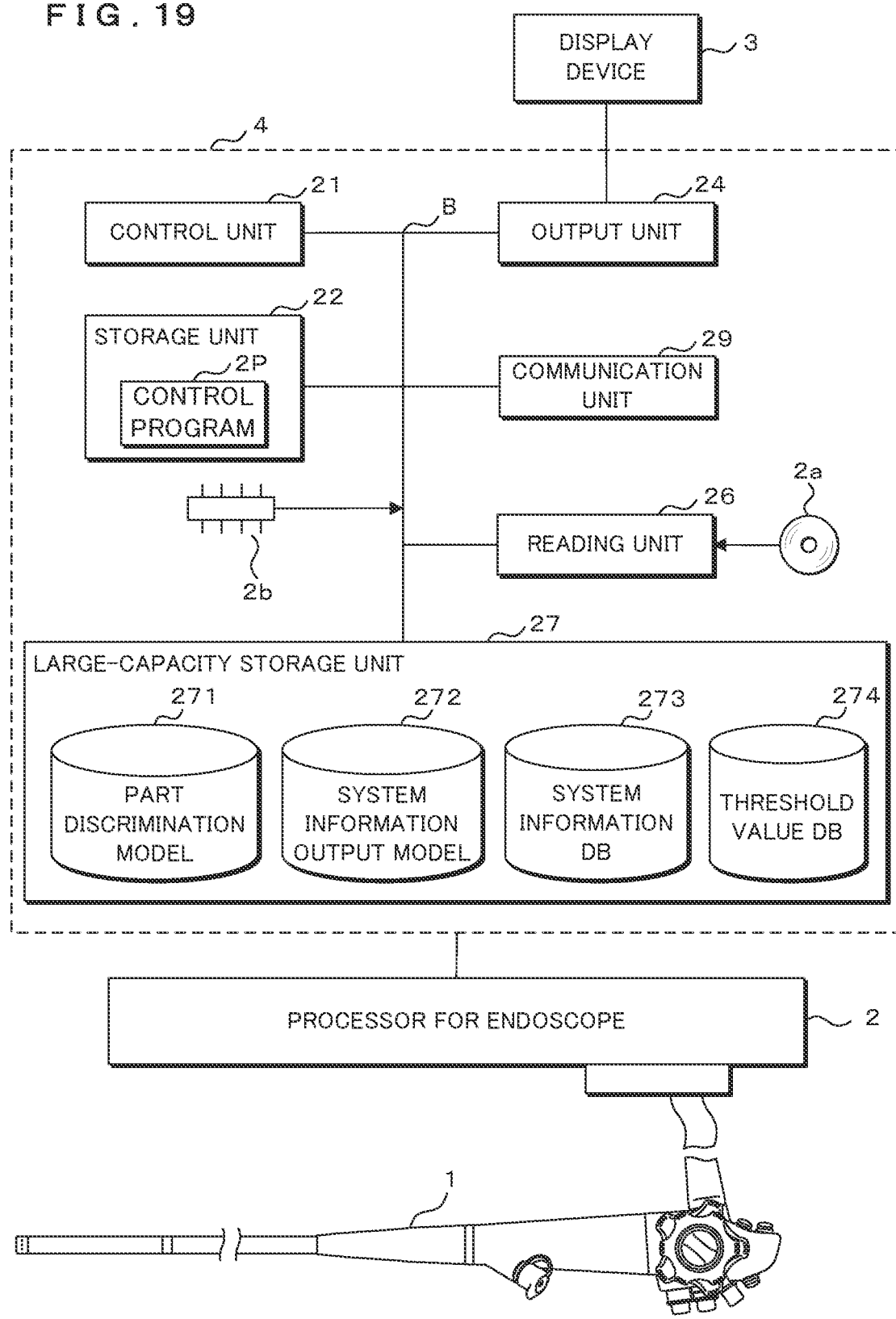
FIG. 19 is a schematic diagram illustrating an example of the configuration of an endoscope system according to Embodiment 4.

FIG. 19 is a schematic diagram illustrating an example of the configuration of an endoscope system according to Embodiment 4. In addition, the same content as that in FIGS. 1 and 3 is denoted by the same reference numeral, and the description thereof will not be repeated. The system illustrated in FIG. 19 includes an endoscope 1, a processor 2, a display device 3, and the information processing device 4. Each device transmits and receives electric signals, video signals, and the like through connectors.

The processor 2 acquires the first system information set in the endoscope system in use, the type information of the endoscope which has been stored in the endoscope 1 in advance, and the endoscopic image captured using the first system information. The processor 2 outputs the acquired first system information, type information, and endoscopic image to the information processing device 4.

A control unit 21 of the information processing device 4 discriminates the part of the subject using the part discrimination model 271 that outputs the discrimination result of discriminating the part of the subject in a case in which the endoscopic image and the type information are input. In addition, since a part discrimination process is the same as that in Embodiment 1 or 2, the description thereof will not be repeated. The control unit 21 acquires a setting image associated with the discriminated part of the subject. Further, since a setting image acquisition process is the same as that in Embodiment 1 or 2, the description thereof will not be repeated.

The control unit 21 acquires the second system information, using the system information output model 272 that outputs the second system information in a case in which the acquired setting image, the type information, and the part of the subject discriminated by the part discrimination model 271 are input. In addition, since a process of acquiring the second system information is the same as that in Embodiment 1 or 2, the description thereof will not be repeated.

The control unit 21 acquires the first system information from the system information DB 273 of the large-capacity storage unit 27. The control unit 21 compares the acquired first system information with the second system information to determine the difference. In a case in which the control unit 21 determines that the two information items are not matched with each other, it outputs a system setting change notification and the second system information to the processor 2.

The processor 2 changes the system setting using the second system information output from the information processing device 4 in response to the system setting change notification output from the information processing device 4. The processor 2 outputs the result (for example, success or failure) of changing the system settings to the information processing device 4. The control unit 21 of the information processing device 4 outputs the notification to the display device 3 according to the setting change result output from the processor 2.

Figure 20:
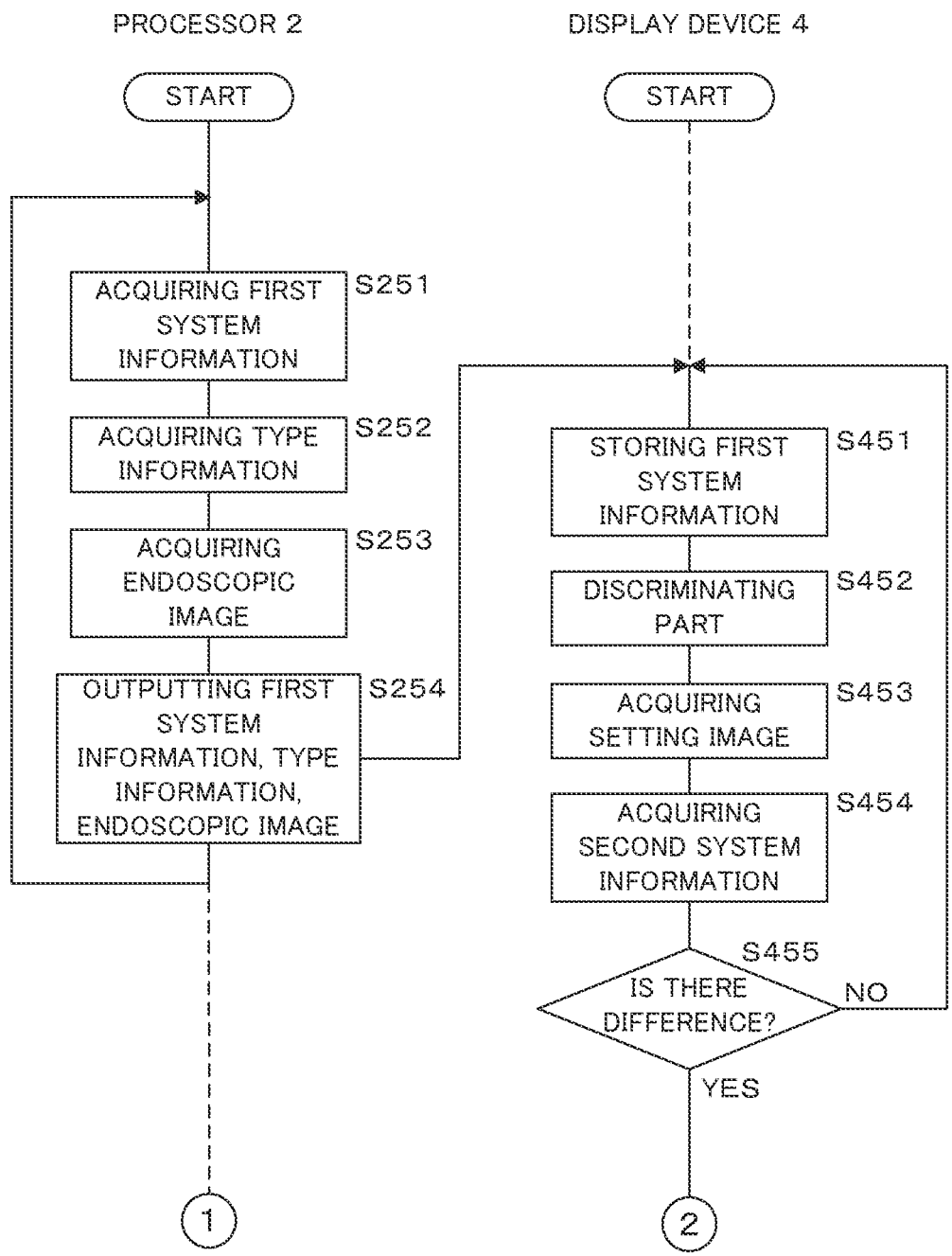
FIG. 20 is a flowchart illustrating a processing procedure when the system settings are automatically adjusted by an information processing device.
Figure 21:
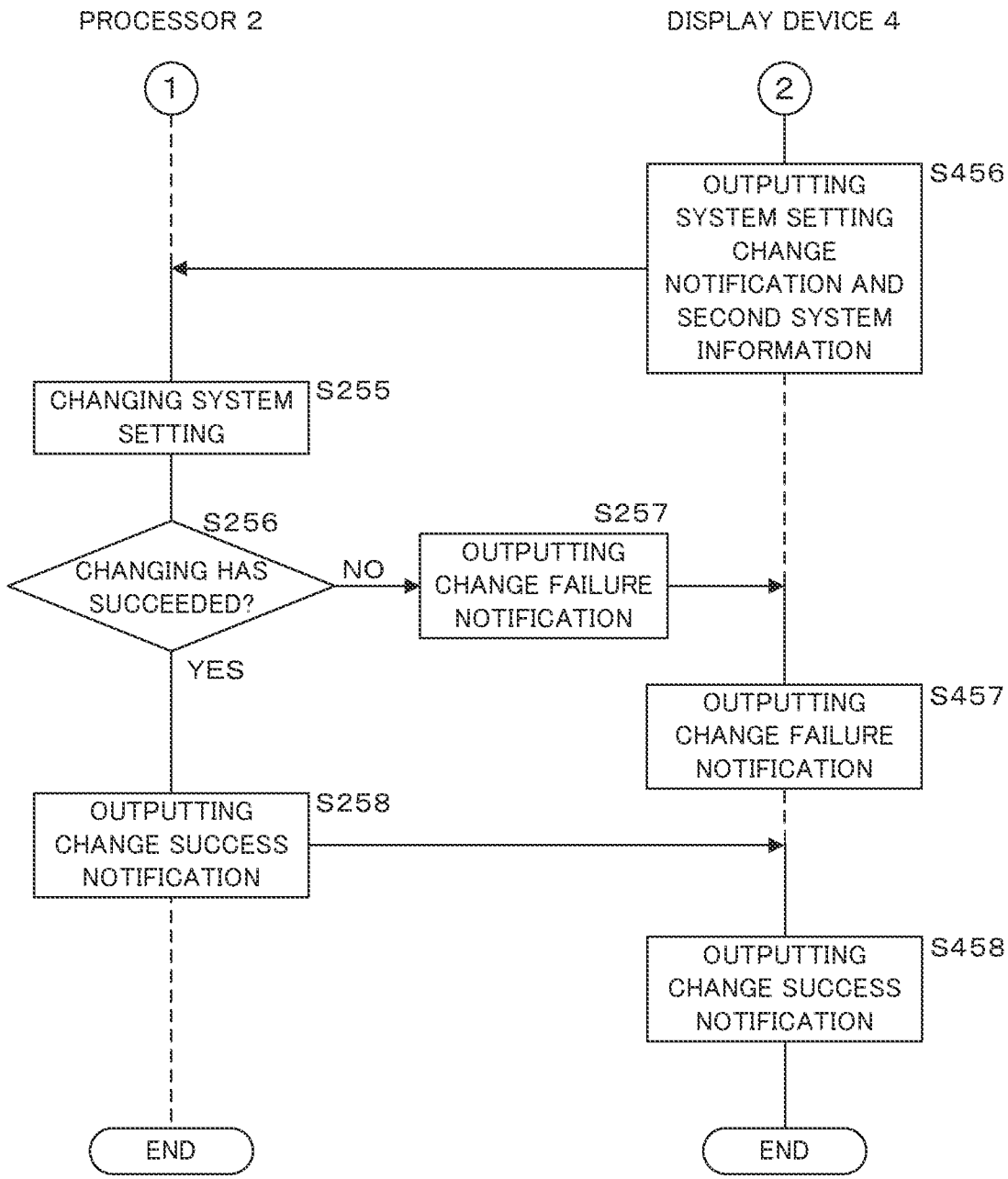
FIG. 21 is a flowchart illustrating a processing procedure when the system settings are automatically adjusted by the information processing device.

FIGS. 20 and 21 are flowcharts illustrating a processing procedure when the information processing device 4 automatically adjusts the system settings. The processor 2 acquires the first system information stored in the endoscopic system in use (Step S251). The control unit 21 acquires the type information of the endoscope stored in the endoscope 1 in advance (Step S252).

The processor 2 acquires the endoscopic image captured using the first system information from the endoscope 1 (Step S253). The processor 2 outputs the acquired first system information, type information, and endoscopic image to the information processing device 4 (Step S254). The processor 2 returns to Step S251. The control unit 21 of the information processing device 4 stores the first system information output from the processor 2 in the system information DB 273 of the large-capacity storage unit 27 (Step S451).

In addition, in this embodiment, the processor 2 outputs the first system information and the type information to the information processing device 4. However, the disclosure is not limited thereto. For example, the first system information and the type information may be stored in advance in the storage unit 22 or the large-capacity storage unit 27 of the information processing device 4.

The control unit 21 of the information processing device 4 discriminates the part of the subject using the part discrimination model 271 that outputs the discrimination result of discriminating the part of the subject in a case in which the endoscopic image and the type information are input (Step S452). The control unit 21 acquires a setting image associated with the discriminated part of the subject (Step S453). The control unit 21 acquires the second system information, using the system information output model 272 that outputs the second system information in a case in which the acquired setting image, the type information, and the part of the subject discriminated by the part discrimination model 271 are input (Step S454).

The control unit 21 compares each item of the first system information with each corresponding item of the second system information to determine the difference (Step S455). In a case in which the control unit 21 determines that there is no difference between the first system information and the second system information (NO in Step S455), it returns to Step S451. In a case in which the control unit 21 determines that there is a difference between the first system information and the second system information (YES in Step S455), it outputs a system setting change notification and the second system information to the processor 2 (Step S456).

The processor 2 changes the system setting using the second system information output from the information processing device 4 in response to the system setting change notification output from the information processing device 4 (Step S255). The processor 2 determines whether the change of the system settings has succeeded or failed (Step S256).

In a case in which the processor 2 determines that the change of the system settings has not succeeded (NO in Step S256), it outputs a change failure notification to the information processing device 4 (Step S257). The control unit 21 of the information processing device 4 outputs the change failure notification output from the processor 2 to the display device 3 (Step S457).

In a case in which the processor 2 determines that the change of the system settings has succeeded (YES in Step S256), it outputs a change success notification to the information processing device 4 (Step S258). The control unit 21 of the information processing device 4 outputs the change success notification output from the processor 2 to the display device 3 (Step S458).

According to this embodiment, the information processing device 4 automatically adjusts the system settings using the learning model. Therefore, the processor 2 does not perform various processes, such as calculation or determination, and it is possible to reduce the load on the processor 2.

Embodiment 5

FIG. 22 is a functional block diagram illustrating the operation of the processor 2 according to Embodiments 1 to 3. The control unit 21 executes the control program 2P such that the processor 2 operates as follows. In addition, the functional block diagram illustrating the operation is similarly applied to the information processing device 4 according to Embodiment 4.

An image acquisition unit 20a acquires the endoscopic image captured using the first system information. A first learning model 20b outputs the discrimination result of discriminating the part of the subject in a case in which the endoscopic image acquired by the image acquisition unit 20a is input. A setting image acquisition unit 20c acquires a setting image associated with the discrimination result output by the first learning model 20b.

A second learning model 20d outputs the second system information in a case in which the setting image acquired by the setting image acquisition unit 20c and the discrimination result output by the first learning model 20b are input. A first calculation unit 20e calculates the parameter on the basis of the endoscopic image acquired by the image acquisition unit 20a. A second calculation unit 20f calculates the parameter on the basis of the setting image acquired by the setting image acquisition unit 20c.

A type information acquisition unit 20g acquires the type information of the endoscope. A change unit 20h changes the system setting on the basis of the second system information output by the second learning model 20d. A determination unit 20i determines the difference between the second system information output by the second learning model 20d and the first system information.

Embodiment 5 is as described above, and the other configurations are the same as those of Embodiments 1 to 4. Therefore, the corresponding portions are denoted by the same reference numerals, and the detailed description thereof will not be repeated.

It is to be noted that, as used herein and in the appended claims, the singular forms "a", "an", and "the" include plural referents unless the context clearly dictates otherwise.

It is to be noted that the disclosed embodiment is illustrative and not restrictive in all aspects. The scope of the present invention is defined by the appended claims rather than by the description preceding them, and all changes that fall within metes and bounds of the claims, or equivalence of such metes and bounds thereof are therefore intended to be embraced by the claims.

The invention claimed is:

1. A processor for an endoscope for determining whether current endoscope settings are the same as a user's favorite endoscope settings, and if not, changing the current endoscope settings to the user's favorite endoscope settings, comprising:
   a controller executing program code to perform:
      acquiring, by the controller, an endoscopic image of a part of a subject captured using current endoscope settings including first system information setting at least two of
         an intensity of a color of light produced by a light source of the endoscope to image the part of the subject,
         a brightness of the light source, and
         an enhancement mode for enhancing the endoscopic image;
      identifying an organ of the subject contained in the acquired endoscopic image with the current endoscope settings using a first learning model that outputs a discrimination result identifying the organ of the subject in a case in which the acquired endoscopic image is input;
      acquiring, by the controller, a setting image of the identified organ of the subject stored in advance in a database before the endoscopic image is acquired, produced by the endoscope using the user's favorite endoscope settings, and associated with the discrimination result output by the first learning model;
      outputting second system information
         containing the user's favorite endoscope settings for the identified organ, setting at least two of the intensity of the color of the light produced by the light source, the brightness of the light source, and the enhancement mode, and produced using a second learning model that outputs the second system information in a case in which the acquired setting image and the part of the subject are input;
comparing the current endoscope settings of the current first system information with the favorite endoscope settings of the second system information;
determining if the difference between the current endoscope settings and the favorite endoscope settings is equal to or greater than a threshold;
changing the endoscope settings to be the favorite endoscope settings when the comparing operation determines that the difference between the current endoscope settings and the favorite endoscope settings is equal to or greater than the threshold;
determining whether the change of the endoscope settings has succeeded;
outputting a failure notification to a display to display the failure notification when the change of endoscope settings has failed;
displaying the failure notification on the display when the failure notification is output to the display;
outputting a success notification to the display to display the success notification when the change of endoscope settings has succeeded; and
displaying the success notification on the display when the success notification is output to the display.

2. The processor for an endoscope according to claim 1, further comprising:
calculating, by the controller, a parameter on the basis of the endoscopic image acquired by the controller,
wherein the first learning model outputs the discrimination result of discriminating a part of a subject in a case in which the parameter calculated by the controller is input.

3. The processor for an endoscope according to claim 2, further comprising:
acquiring, by the controller, type information of an endoscope,
wherein the first learning model outputs the discrimination result of discriminating a part of a subject in a case in which the type information acquired by the controller and the parameter calculated by the controller are input.

4. The processor for an endoscope according to claim 2, wherein the parameter include an average value of R, G, or B pixels values of pixels constituting the endoscopic image.

5. The processor for an endoscope according to claim 1, further comprising:
calculating, by the controller, a parameter on the basis of the setting image acquired by the controller,
wherein the second learning model outputs the second system information in a case in which the parameter calculated by the controller and the discrimination result output by the first learning model are input.

6. The processor for an endoscope according to claim 5, further comprising:
acquiring, by the controller, type information of an endoscope,
wherein the second learning model outputs the second system information in a case in which the type information acquired by the controller, the parameter calculated by the controller, and the discrimination result output by the first learning model are input.

7. An endoscope system for determining whether current endoscope settings are the same as a user's favorite endoscope settings, and if not, changing the current endoscope settings to the user's favorite endoscope settings, comprising:
a processor for an endoscope; and
an endoscope that is connected to the processor for the endoscope, wherein the processor for the endoscope includes a controller executing program code to perform:
acquiring, by the controller, an endoscopic image of a part of a subject captured using current endoscope settings including first system information setting at least two of
an intensity of a color of light produced by a light source of the endoscope to image the part of the subject,
a brightness of the light source, and
an enhancement mode for enhancing the endoscopic image;
identifying an organ of the subject contained in the acquired endoscopic image with the current endoscope settings using a first learning model that outputs a discrimination result of identifying the organ of the subject in a case in which the acquired endoscopic image is input;
acquiring, by the controller, a setting image of the identified organ of the subject stored in advance in a database before the endoscopic image is acquired, produced by the endoscope using the user's favorite endoscope settings, and associated with the discrimination result output by the first learning model;
outputting second system information
containing the user's favorite endoscope settings for the identified organ, setting at least two of the intensity of the color of the light produced by the light source, the brightness of the light source, and the enhancement mode, and
produced using a second learning model that outputs the second system information in a case in which the acquired setting image and the part of the subject are input;
comparing the current endoscope settings of the current first system information with the favorite endoscope settings of the second system information;
determining if the difference between the current endoscope settings and the favorite endoscope settings is equal to or greater than a threshold;
changing the endoscope settings to be the favorite endoscope settings when the comparing operation determines that the difference between the current endoscope settings and the favorite endoscope settings is equal to or greater than the threshold;
determining whether the change of the endoscope settings has succeeded;
outputting a failure notification to a display to display the failure notification when the change of endoscope settings has failed;
displaying the failure notification on the display when the failure notification is output to the display;
outputting a success notification to the display to display the success notification when the change of endoscope settings has succeeded; and
displaying the success notification on the display when the success notification is output to the display.

8. An information processing apparatus for determining whether current endoscope settings are the same as a user's favorite endoscope settings, and if not, changing the current endoscope settings to the user's favorite endoscope settings, comprising one or a plurality of processors, the one or the plurality of processors executing the following processing of:

acquiring an endoscopic image of a part of a subject captured using current endoscope settings including first system information setting at least two of
an intensity of a color of light produced by a light source of the endoscope to image the part of the subject,
a brightness of the light source, and
an enhancement mode for enhancing the endoscopic image;
identifying an organ of the subject contained in the acquired endoscopic image with the current endoscope settings using a first learning model that outputs a discrimination result of identifying the organ of the subject in a case in which the acquired endoscopic image is input;
acquiring a setting image of the identified organ of the subject stored in advance in a database before the endoscopic image is acquired,
produced by the endoscope using the user's favorite endoscope settings, and
associated with the discrimination result output by the first learning model;
outputting second system information
containing the user's favorite endoscope settings for the identified organ, setting at least two of the intensity of the color of the light produced by the light source, the brightness of the light source, and the enhancement mode, and
produced using a second learning model that outputs the second system information in a case in which the acquired setting image and the part of the subject are input;
comparing the current endoscope settings of the current first system information with the favorite endoscope settings of the second system information;
determining if the difference between the current endoscope settings and the favorite endoscope settings is equal to or greater than a threshold;
changing the endoscope settings to be the favorite endoscope settings when the comparing operation determines that the difference between the current endoscope settings and the favorite endoscope settings is equal to or greater than the threshold;
determining whether the change of the endoscope settings has succeeded;
outputting a failure notification to a display to display the failure notification when the change of endoscope settings has failed;
displaying the failure notification on the display when the failure notification is output to the display;
outputting a success notification to the display to display the success notification when the change of endoscope settings has succeeded; and
displaying the success notification on the display when the success notification is output to the display.

9. A non-transitory computer-readable storage medium storing a program that causes a computer to perform a process endoscope for determining whether current endoscope settings are the same as a user's favorite endoscope settings, and if not, changing the current endoscope settings to the user's favorite endoscope settings, comprising:

acquiring an endoscopic image of a part of a subject captured using current endoscope settings including first system information setting at least two of
an intensity of a color of light produced by a light source of the endoscope to image the part of the subject,
a brightness of the light source, and
an enhancement mode for enhancing the endoscopic image;
identifying an organ of the subject contained in the acquired endoscopic image with the current endoscope settings using a first learning model that outputs a discrimination result of identifying the organ of the subject in a case in which the acquired endoscopic image is input;
acquiring a setting image of the identified organ of the subject
stored in advance in a database before the endoscopic image is acquired,
produced by the endoscope using the user's favorite endoscope settings, and
associated with the discriminated part of the subject;
outputting second system information
containing the user's favorite endoscope settings for the identified organ, setting at least two of the intensity of the color of the light produced by the light source, the brightness of the light source, and the enhancement mode, and
produced using a second learning model that outputs the second system information in a case in which the acquired setting image and the part of the subject are input;
comparing the current endoscope settings of the current first system information with the favorite endoscope settings of the second system information;
determining if the difference between the current endoscope settings and the favorite endoscope settings is equal to or greater than a threshold;
changing the endoscope settings to be the favorite endoscope settings when the comparing operation determines that the difference between the current endoscope settings and the favorite endoscope settings is equal to or greater than the threshold;
determining whether the change of the endoscope settings has succeeded;
outputting a failure notification to a display to display the failure notification when the change of endoscope settings has failed;
displaying the failure notification on the display when the failure notification is output to the display;
outputting a success notification to the display to display the success notification when the change of endoscope settings has succeeded; and
displaying the success notification on the display when the success notification is output to the display.

10. An information processing method for determining whether current endoscope settings are the same as a user's favorite endoscope settings, and if not, changing the current endoscope settings to the user's favorite endoscope settings, comprising:

acquiring an endoscopic image of a part of a subject captured using current endoscope settings including first system information setting at least two of
an intensity of a color of light produced by a light source of the endoscope to image the part of the subject,
a brightness of the light source, and an enhancement mode for enhancing the endoscopic image;

identifying an organ of the subject contained in the acquired endoscopic image with the current endoscope settings using a first learning model that outputs a discrimination result of identifying the organ of the subject in a case in which the acquired endoscopic image is input;

acquiring a setting image of the identified organ of the subject stored in advance in a database before the endoscopic image is acquired,
- produced by the endoscope using the user's favorite endoscope settings, and
- associated with the discriminated part of the subject;

outputting second system information
- containing the user's favorite endoscope settings for the identified organ, setting at least two of the intensity of the color of the light produced by the light source, the brightness of the light source, and the enhancement mode, and
- produced using a second learning model that outputs the second system information in a case in which the acquired setting image and the part of the subject are input;

comparing the current endoscope settings of the current first system information with the favorite endoscope settings of the second system information;

determining if the difference between the current endoscope settings and the favorite endoscope settings is equal to or greater than a threshold;

changing the endoscope settings to be the favorite endoscope settings when the comparing operation determines that the difference between the current endoscope settings and the favorite endoscope settings is equal to or greater than the threshold;

determining whether the change of the endoscope settings has succeeded;

outputting a failure notification to a display to display the failure notification when the change of endoscope settings has failed;

displaying the failure notification on the display when the failure notification is output to the display:

outputting a success notification to the display to display the success notification when the change of endoscope settings has succeeded; and displaying the success notification on the display when the success notification is output to the display.

* * * * *